(12) United States Patent
Shea

(10) Patent No.: US 8,802,056 B2
(45) Date of Patent: Aug. 12, 2014

(54) METHOD FOR TESTING AND TREATING DELAYED FOOD ALLERGIES

(76) Inventor: John Shea, Burleson, TX (US)

( * ) Notice: Subject to any disclaimer, the term of this patent is extended or adjusted under 35 U.S.C. 154(b) by 452 days.

(21) Appl. No.: 13/003,999

(22) PCT Filed: Jul. 17, 2009

(86) PCT No.: PCT/US2009/051025
§ 371 (c)(1),
(2), (4) Date: Jan. 13, 2011

(87) PCT Pub. No.: WO2010/009417
PCT Pub. Date: Jan. 21, 2010

(65) Prior Publication Data
US 2011/0150776 A1   Jun. 23, 2011

Related U.S. Application Data

(60) Provisional application No. 61/081,513, filed on Jul. 17, 2008.

(51) Int. Cl.
*A61K 39/35* (2006.01)
*A61K 36/00* (2006.01)

(52) U.S. Cl.
USPC ............. 424/9.2; 424/9.1; 424/725; 436/8; 436/20

(58) Field of Classification Search
USPC ................. 424/9.2, 9.1, 725; 436/8, 20
See application file for complete search history.

(56) References Cited

U.S. PATENT DOCUMENTS

| | | |
|---|---|---|
| 6,429,189 B1 | 8/2002 | Borodic |
| 2002/0150537 A1* | 10/2002 | Val et al. .................. 424/9.2 |
| 2005/0042243 A1 | 2/2005 | Redmond et al. |
| 2005/0158325 A1* | 7/2005 | Hammerbeck et al. ..... 424/155.1 |
| 2006/0013773 A1* | 1/2006 | Power .................. 424/9.81 |
| 2006/0121064 A1 | 6/2006 | Brimnes et al. |

OTHER PUBLICATIONS

Miranowski et al. Unproved Methods and Theories in Allergy; Allergy and Asthma Proceedings, 2004, vol. 25, No. 4, pp. 61-63(3) pp. S61-S63.*
Metcalfe, Dean, MD A Current Practical Approace to the Diagnosis of Suspected Adverse Reactions to Foods; NER Allergy Proc., Jan.-Feb. 1987, vol. 8, No. 1, pp. 22-26.*
NESA Proceedings; various Authors, Position Statements of the Americal Academy of Allergy; Summer 1981; vol. 2, No. 3, pp. 164-170.*
International Search Report and Written Opinion mailed by ISA/US on Aug. 31, 2009 for PCT/US09/51025.
International Preliminary Report on Patentability mailed by IPEA/US on Nov. 23, 2010 for PCT/US09/51025.
Mirandowski et al. Unproved Methods and Theories in Allergy, Allergy and Asthma Proceedings, 2004, vol. 25, No. 4, pp. 61-63(3), p. 61, col. 1, para 2.

* cited by examiner

*Primary Examiner* — Patricia Leith
(74) *Attorney, Agent, or Firm* — James E. Walton; Damon R. Hickman

(57) ABSTRACT

A method for testing, treating, and preventing delayed food allergies includes: receiving detailed symptom, medical, and dietary histories from a patient; formulating a combination of one or more food extracts at selected concentration for sublingual administration over a trial period; determining whether the patient's symptoms have improved, worsened, or had no change, in response to the administration of the combination; and altering the combination in response to whether the patient's symptoms have improved, worsened, or not changed, so as to induce immune system food tolerance.

14 Claims, 21 Drawing Sheets

SUPER-COMBO VIAL FOOD EXTRACTS
(EACH EXTRACT 1/25 CONCENTRATION)

BASIC VIAL FOOD EXTRACTS
(EACH EXTRACT 1/25 CONCENTRATION)

SUPER-COMBO VIAL FOOD EXTRACTS
(EACH EXTRACT 1/25 CONCENTRATION)

BASIC VIAL FOOD EXTRACTS
(EACH EXTRACT 1/25 CONCENTRATION)

**ULTRA-COMBO VIAL FOOD EXTRACTS
(EACH EXTRACT 1/25 CONCENTRATION)**

**DRINK-COMBO VIAL FOOD EXTRACTS
(EACH EXTRACT 1/25 CONCENTRATION)**

BEER VIAL FOOD EXTRACTS
(EACH EXTRACT 1/25
CONCENTRATION)

WINE VIAL FOOD EXTRACTS
(EACH EXTRACT 1/25
CONCENTRATION)

GOT VIAL FOOD EXTRACTS
(EACH EXTRACT 1/25
CONCENTRATION)

1200

FOOD SENSITIVITY QUESTIONNAIRE

| | | |
|---|---|---|
| 1 | Nose blocks trying to sleep: How many years? _____ | |
| | a. right side? _____ | |
| | b. left side? _____ | |
| | c. both sides? _____ | |
| | d. switches sides? _____ | |
| | e. down side blocks? _____ | |
| | | |
| 2 | Nasal blockage while asleep causes you to: | |
| | a. Mouth breathe? _____ | |
| | b. Drool? _____ | |
| | c. Snore sometimes? _____ | |
| | d. Wake for water? _____ times per night | |
| | | |
| 3 | Sneeze several times in a row: | |
| | a. _____ times a day? | |
| | b. _____ times a week? | |
| | c. How many times in a row? _____ | |
| | d. After meals? _____ | |
| | | |
| 4 | Itching: | |
| | a. In the inner corner of the eye? _____ | |
| | b. Deep in the ear / throat? _____ | |
| | c. Skin? _____ | |
| | d. Rash? _____ | |
| | e. Eczema? _____ | |
| | | |
| 5 | Headache: How many years? _____ | |
| | a. Daily? _____ | |
| | b. Weekly? _____ | |
| | c. Monthly? _____ | |
| | d. With periods? _____ | |
| | e. Migraine: How many years? _____ | |
| |     i. With fuzzy vision first? _____ | |
| |     ii. With nausea? _____ | |
| |     iii. With sensitivity to light? _____ | |
| |     iv. With sensitivity to noise? _____ | |
| | f. Middle of the night? _____ | |
| | g. Take migraine medication? _____ | |
| | h. Take pain medication? _____ | |
| | i. Average monthly cost to treat $_____ | |
| | | |
| 6 | Dark circles under the eyes? _____ | |

FOOD SENSITIVITY QUESTIONNAIRE (CONT)

| | |
|---|---|
| 7 | Asthma: How many years? _____ |
| | a. Daily? _____ |
| | b. Weekly? _____ |
| | c. Monthly? _____ |
| | d. Few times a year? _____ |
| | e. With exercise? _____ |
| | f. Average monthly cost to treat: $_____ |
| 8 | Tried treatments: |
| | a. Decongestant spray? _____ |
| | b. Decongestant oral medication? _____ |
| | c. Steroid nasal spray? _____ |
| | d. Nasal strips? _____ |
| | e. Sinus Surgery? _____ |
| |    i. Nasal polyps? _____ |
| | f. Average monthly cost to treat: $_____ |
| 9 | Crave foods: |
| | a. Milk / Cheese? _____ |
| | b. Coffee? _____ |
| | c. Chewing gum? _____ |
| | d. Sugar free products? _____ |
| | e. Ketchup / salsa? _____ |
| | f. Bread? _____ |
| 10 | Picky eater: |
| | a. Like only certain foods? _____ |
| | b. Don't like vegetables except corn? _____ |
| | c. Snack after dinner? _____ |
| | d. Eat or drink in middle of night? _____ |
| 11 | Crave drinks: |
| | a. Tea? _____ |
| | b. Dr. Pepper? _____ |
| | c. Other cola? _____ |
| | d. Diet drinks? _____ |
| | e. Beer? _____ |
| | f. Wine? _____ |
| | g. Liquor? _____ |
| 11. | As a baby you had colic? _____ |
| 12 | List known problem foods and reactions: |

DELAYED FOOD ALLERGY EVALUATION GUIDE

<u>If your problems occur all year, indoors or out, enter:</u>
<u>1 = slight,   2 = moderate,   3= severe</u>

At night when lying flat, nasal blockage worsens   ___
    Nasal lockage switches from side to side, with the down side worse   ___
    Drool spots on pillow   ___
    Wake with a dry mouth; water at bedside   ___

Repeated sneezing several times in a row   ___

Runny nose   ___

Itching of inner corner of eye, deep in the ear, or in the throat   ___

Throat clearing   ___

Headaches / migraines   ___

Cough   ___

Skin itching / rash   ___

Food craving, especially milk / cheese, chocolate, drinks, gum, etc.   ___

Dependent on decongestant nose spray, oral decongestants   ___

Asthma with exercise   ___

Asthma without exercise   ___

Chronic sinus infections   ___

Nasal polyps   ___

Fatigue episodes   ___

Snoring episodes   ___

<u>TOTAL SCORE</u>   ====

| PATIENT NAME _____ DATE _____ |

SUBLINGUAL FOOD DROP GUIDE

1) One drop is placed under the tongue and left there at least 15 seconds, three times a day: when you awaken, at bedtime, and in the afternoon.

2) Should symptoms worsen during the first few days, please stop the drops and call the office for a weaker vial.

CIRCLE SYMPTOM CHANGE AND KEEP FOR YOUR NEXT VISIT

| | | | |
|---|---|---|---|
| WORSE | NO CHANGE | BETTER | ------ FATIGUE |
| WORSE | NO CHANGE | BETTER | ------ ALTERNATING NASAL BLOCKAGE |
| WORSE | NO CHANGE | BETTER | ------ WAKING WITH DRY MOUTH |
| WORSE | NO CHANGE | BETTER | ------ SNORING |
| WORSE | NO CHANGE | BETTER | ------ DROOLING ON PILLOW |
| WORSE | NO CHANGE | BETTER | ------ REPEATED SNEEZING |
| WORSE | NO CHANGE | BETTER | ------ RUNNY NOSE |
| WORSE | NO CHANGE | BETTER | ------ NASAL ITCHING |
| WORSE | NO CHANGE | BETTER | ------ INNER CORNER EYE ITCHING |
| WORSE | NO CHANGE | BETTER | ------ THROAT CLEARING OR ITCHING |
| WORSE | NO CHANGE | BETTER | ------ DEEP EAR ITCHING |
| WORSE | NO CHANGE | BETTER | ------ SKIN ITCHING / RASH |
| WORSE | NO CHANGE | BETTER | ------ WHEEZING |
| WORSE | NO CHANGE | BETTER | ------ COUGH |
| WORSE | NO CHANGE | BETTER | ------ HEADACHE |
| WORSE | NO CHANGE | BETTER | ------ MIGRAINE |
| WORSE | NO CHANGE | BETTER | ------ DIZZINESS |
| WORSE | NO CHANGE | BETTER | ------ TINNITUS / EAR BUZZING |
| WORSE | NO CHANGE | BETTER | ------ IRRITABILITY |
| WORSE | NO CHANGE | BETTER | ------ HYPERACTIVITY |
| WORSE | NO CHANGE | BETTER | ------ JOINT STIFFNESS |
| WORSE | NO CHANGE | BETTER | ------ ABDOMINAL BLOATING |
| WORSE | NO CHANGE | BETTER | ------ IRRITABLE BOWEL |

```
SUBLINGUAL MANAGEMENT STRATEGIES
FOR FOOD SENSITIVITY (DELAYED FOOD ALLERGY)
```

1. Patient identification
   a. Questionnaire
   b. Physical exam
2. IgE blood tests
   a. Asthma
   b. History of immediate allergy
      i. Swelling
      ii. Shortness of breath
      iii. Hives
3. SLIT trial dilution selection
4. SLIT trial two weeks
   a. Abort if symptoms worse in first 3 days: select weaker dilution
   b. Select stronger dilution if no response
   c. Select different food combination if still no response
   d. Elimination diet if still no response
5. Same, after all trials
   a. Diet change
6. Better
   a. Four month treatment and return to re-evaluate
7. Worse
   a. Symptomatic with each vial trial: consider glycerin sensitivity
   b. Symptomatic during 1st 3 days, then symptoms clear after stopping:
      i. Try weaker dilutions
8. Encourage limiting "favorites" and rotating diet; find new foods
9. Avoid gum, mints, candies, tobacco... any habitual food

FIG. 15

| Date | SLIT | % Better | Worse | Same | Comment |
|---|---|---|---|---|---|
| | | | | | |

SLIT LOG    Name _____

FIG. 16

METHOD FOR TESTING AND TREATING DELAYED FOOD ALLERGIES

TECHNICAL FIELD

The present application relates to delayed food allergy treatment, in particular, using sublingual drops to test, treat, and prevent delayed food allergies.

DESCRIPTION OF THE PRIOR ART

Beginning in the early 1900's, the term "allergy" was used to denote a generic immune response. Then, in the early 1960's, based upon advancements in the identification and understanding of the antibody Immunoglobulin E (IgE), Dr. Phillip Gell and Dr. Robin Coombs developed the well-known Gell and Coombs Classification System, in which immune mechanisms of tissue injury are classified into four types of reactions, based upon the immunopathological damage done: Type I—Immediate Hypersensitivity; Type II—Cytotoxic Hypersensitivity; Type III—Immune Complex; and Type IV—Delayed Type Hypersensitivity. According to Drs. Gell and Coombs, only immune reactions involving the IgE antibody should be referred to as "allergies." Type I reactions are considered related to IgE, while Type II-IV reactions are generally considered non-IgE mediated reactions.

Although the Gell and Coombs Classification System has become widely accepted, many physicians and lay people use the term "allergy" to denote any adverse immune response, i.e., Type I, II, III, or IV. One reason for this continued use of the term "allergy" to refer to all four types of reactions is that although IgE reactions are present in life-threatening reactions, such as to food, IgE reactions are also present in typical seasonal reactions to pollens and molds, and in reactions to mites and animal dander. Typically, Type I reactions are sudden. Some Type I reactions may result in life-threatening symptoms. Other Type I reactions produce chronic symptoms, such as reactions to ragweed.

A "delayed food allergy" is a chronic reaction to a food or foods that would not normally occur in most people. Delayed food allergies have been described in many ways, including: food sensitivities, chronic delayed food hypersensitivities, chronic food allergies, hidden food allergies, and food allergy-addictions. Delayed food allergies, which are typically classified as Gell and Coombs Type IV reactions, typically do not include immediate food allergies to specific, known foods, which can result in anaphylaxis and death, such as an acute peanut allergy or other Gell and Coombs Type I reactions.

There are many types of delayed food allergies. Delayed food allergies are caused by a wide variety of foods and bring about a wide variety of signs and symptoms. One sign of a delayed food allergy is dark circles under the eyes. Symptoms include: mental and physical fatigue, alternating dependent nocturnal nasal blockage, waking with a dry mouth, snoring, drooling while asleep, deep ear itching, persistent runny and itchy nose, chronic throat clearing, migraine and common headaches, repeated sneezing, rhinitis-induced sinus and ear infections, skin itching and hives, cough, wheezing, exercise-induced asthma, intermittent tinnitus/hearing loss, hyperactivity, abdominal bloating, and irritable bowel.

There are many different methods of testing for allergens that trigger delayed food allergies. Some tests are designed only for inhalant allergens, some tests are designed only for food allergens, and some tests are designed to test both types of allergens. For example, intracutaneous skin tests using dilutions of common airborne allergens are commonly used to test for inhalant allergens. However, with intracutaneous skin tests, the airborne allergens are uncommonly mixed into a single solution. In addition, intracutaneous skin tests are used to test for immediate food allergies, but only with great caution, starting with weak dilutions. This is because the risk of potentially lethal anaphylactic reactions is too high. For those patients who have IgE mediated allergies, the radio-allergosorbent (RAST) test can be used. The RAST test measures the allergen-specific IgE antibodies in a patient's blood. Other types of blood tests such as serum IgG and ALCAT have had limited usefulness because of poor specificity to detect delayed food allergies, or food sensitivities. Other methods for testing delayed food allergies include: elimination diets, rotation diets, and provocation/neutralization (P/N) tests. These tests also have limited usefulness, primarily due to difficulty in making any significant changes in a patient's diet.

The elimination diet is often used to identify delayed food allergies. The elimination diet requires a patient suffering from delayed food allergies to eliminate certain foods or classes of foods from the patient's diet, and then slowly reintroduce each food type, in an attempt to identify the food allergen. Typically, a suspected food is removed from the patient's diet for four days, reintroduced to the patient's diet, and the patient is monitored for symptoms to reappear over a 24-hour period after reintroduction. This method is difficult to police and extremely taxing to the patient. Moreover, the elimination diet is quite difficult for even the highly motivated patient to successfully perform. The patient is asked to purchase, prepare, and eat foods that are not normally in the patient's diet, and that are often not palatable for the patient with delayed food allergies, who is usually a "picky eater."

The rotation diet is another traditional method of identifying delayed food allergies, particularly in patients with chronic symptoms. In the rotation diet, the suspected food is only ingested every three or four days, then the patient is observed for symptoms within a day.

Provocation/neutralization tests can be done with either intracutaneous injections or sublingual drops. The purpose of the P/N test is to provoke an allergic reaction and then find a neutralizing dose of the allergen. With intracutaneous injections, the patient receives a series of injections, each injection having a different dilution of a suspected allergen. After the injection, the injection site is inspected, and the patient's symptoms are monitored, to determine whether the patient is allergic to the suspected allergen. This process takes a relative long period of time to administer. For example, the patient may have to remain in the physician's office all day, testing a single food every half hour to one hour. In some cases, it can take up to two days for a patient's symptoms to occur and resolve themselves. This is particularly true in instances when the patient has a bad reaction to a test.

Provocation/neutralization tests may also be conducted using sublingual drops. In this method, extracts of certain individual foods at certain concentrations are administered one after another until the allergen is identified by symptom provocation. The extracts used in conventional sublingual testing are obtained by physicians from extract manufacturers in certain standardized concentrations. Commonly a mixture of 50% water and 50% glycerin, by volume. This process is expensive and time consuming. For example, it is not uncommon for a patient to spend an entire day or more at a physician's office or clinic undergoing testing.

Recently, sublingual drops of solutions containing multiple food allergens have become available. However, these solutions are homeopathic, in which the food extracts are at very low concentrations. These remedies are available without a prescription and without the patient undergoing an examination by a physician. In other words, no dietary or medical history is taken to determine if indeed there are symptoms possibly related to food sensitivity, which food extracts to include in the solution, and which concentration of extracts is to be tried.

All too often, patients with delayed food allergies go to their doctors, but do not get any relief of their symptoms. Their doctors often lack the training and experience to offer adequate dietary and medical histories that could uncover symptoms of delayed food allergies, and the patients are told to try to get relief from oral as well as nasal spray decongestants, antihistamines, headache and/or migraine medications, steroid and/or bronchodilator medications for asthma, or go see an allergist. The patient may become "addicted" to decongestant nose spray for many years, with associated side effects. The patient may try to rely upon external nasal strips for relief, with only partial temporary relief of but one of the symptoms of delayed food allergy: nasal congestion. If the patient schedules an appointment with an allergist, the allergist primarily runs tests on inhalant allergens, and only a few skin tests for foods, and is mainly interested in IgE mediated, Type I reactions, and the narrow set of symptoms associated therewith. If the allergist cannot help the patient, the allergist often recommends surgery on the nasal airway and nasal decongestants. This is often because allergists typically do not treat non-IgE mediated disease. These allergists typically classify these patients as having "vasomotor rhinitis" or "perennial non-allergenic rhinitis". The problem with nasal surgery is that if the cause of the problem was a delayed food allergy, the surgery is usually only helpful for a limited time, as the symptoms often begin to return a few months after the surgery. Moreover, the many other symptoms related to delayed food allergies, including those set forth above, are not addressed at all.

Although many attempts to test and treat delayed food allergies have been made, considerable shortcomings remain.

BRIEF DESCRIPTION OF THE DRAWINGS

The novel features believed characteristic in the present application are set forth in the description. However, the application itself, as well as, a preferred mode of use, and further objectives and advantages thereof, will best be understood by reference to the following detailed description when read in conjunction with the accompanying drawings, wherein:

FIGS. 12A and 12B represent a chart showing a Food Sensitivity Questionnaire for use in the method for testing and treating delayed food allergies disclosed in the present application.

FIG. 13 is a chart showing a Delayed Food Allergy Evaluation Guide for use in the method for testing and treating delayed food allergies disclosed in the present application.

FIG. 14 is a chart showing a Sublingual Food Drop Guide for use in the method for testing and treating delayed food allergies disclosed in the present application.

FIG. 15 is a chart showing Sublingual Management Strategies for Food Sensitivity for use in the method for testing and treating delayed food allergies disclosed in the present application.

FIG. 16 is a chart showing a SLIT Log for use in the method for testing and treating delayed food allergies disclosed in the present application.

Figure 1A:
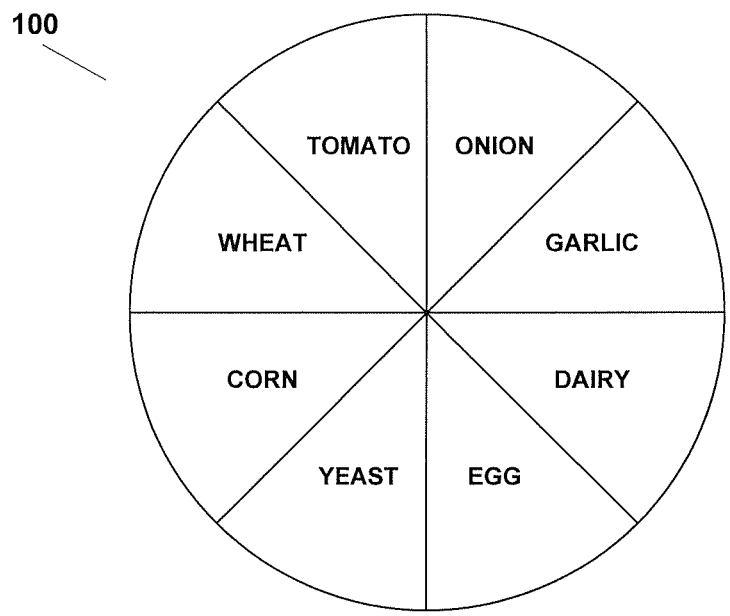
FIG. 1A is a chart showing extracts used in a "super-combo" vial of solution according to the present application.

While the present application is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the present application as described herein.

DESCRIPTION OF THE PREFERRED EMBODIMENT

The present application represents the discovery of a system and method of testing, treating, and preventing delayed food allergies. With the system and method of the present application, delayed food allergies can be identified and treated, while the patient continues to eat the foods he wants. Moreover, the system and method of the present application may be used to prevent certain delayed food allergies from evolving. It should be appreciated that even though the system and method of the present application is tailored towards human patients; the methods disclosed herein can also be applied towards testing, treating, and preventing delayed food allergies in non-humans.

The preferred embodiment of the present application utilizes sublingual drops that target receptors under the tongue called dendritic cells, which detect molecules in an allergy drop solution and present them to immune system T-cells. These regulatory T-cells are thought to induce and maintain tolerance to antigens. The patient commonly notes symptom changes within days of starting a two week trial vial, then usually notes return of symptoms within 2 days.

The food mix in the various allergy drop solutions may contain foods to which the patient is sensitive, as well as foods to which there no sensitivity. These foods to which there is no sensitivity are kept in the treatment vials to help prevent development of future sensitizations. Furthermore, the process of eliminating a common food from the diet is so impractical, that almost all patients are not interested in separating and testing sublingually the individual foods found in the food mixes.

The dietary history is important because what is most often consumed is most often the culprit. However, because the dietary history is imperfect and the food culprit is commonly ingested in a "hidden form", the dietary history is usually of little benefit. Examples of "hidden" foods include onion hidden in ketchup and whey hidden in bread and cereal. The majority of patients with food sensitivities respond to the foods present in the "super-combo" mix.

Illustrative embodiments of the present application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

Referring to FIG. 1A in the drawings, a chart 100 listing the extracts used in the preferred embodiment of a "super-combo" vial of solution according to the present application is shown. Wheat, corn, dairy, egg, yeast, garlic, onion and tomato (WCDEYGOT) are believed to be some of the most common foods that cause chronic food sensitivity.

The WCDEYGOT is administered as food extracts (commonly available food allergy extracts) in a water and glycerin solution, disposed within a dropper vial, in a specific dilution. This solution is referred to as a "super-combo" vial. According to the preferred embodiment, the optimum starting dilution of the present application is determined by using an algorithm based upon patient age, headache and asthma severity: (see Optimum Starting Dilution Algorithm Chart).

Optimum Starting Dilution Algorithm Chart

The optimum starting dilution is the sum of four factors based on age, asthma, headache, and rhinitis:

| AGE + | ASTHMA + | HEADACHE + | RHINITIS | = DILUTION |
|---|---|---|---|---|
| 2-20 = 2 | Mild = 0 | Mild = 0 | Mild = 0 | |
| 30 = 3 | Moderate = 1 | Moderate = 1 | Moderate = 1 | |
| 40 = 4 | Severe = 2 | Severe = 2 | Severe = 2 | |
| 50 = 5 | | | | |
| 60 = 6 | | | | |
| 70 = 7 | | | | |
| 80 = 8 | | | | |
| 90 = 9 | | | | |
| 100 = 10 | | | | |

EXAMPLES 13 year old female with recurrent severe migraine: 2+2=#4 Dilution 63 year old male with mild headache: 6+0=#6 Dilution 29 year old female with asthma treated a few times a year but with rather chronic severe migraine headaches: 2+0+2=#4 Dilution 71 year old male with moderate headaches: 7+1=#8 Dilution 33 year old female with chronic severe asthma and daily severe headache: 3+2+2=#7 Dilution The various dilutions are created by starting with the concentrate provided by the allergy extract company, and making ⅕ dilutions using a diluent comprised of 1 part glycerin and 1 part water, by volume. A number 1 dilution is ⅕ C is created by diluting 1 cc of food extract concentrate with 4 cc of a diluent, by volume. A number 2 dilution is ¹/₂₅ C is realized by diluting 1 cc of ⅕ C solution with 4 cc of the diluent, by volume. A ¹/₁₂₅ C is realized by diluting 1 cc of ¹/₂₅ C solution with 4 cc of the diluent, by volume, and so on for further dilution. (see the DILUTION CHART)

| DILUTION CHART | |
|---|---|
| CONCENTRATE | 1/1 |
| #1 DILUTION | 1/5 |
| #2 DILUTION | 1/25 |
| #3 DILUTION | 1/125 |
| #4 DILUTION | 1/625 |
| #5 DILUTION | 1/3,125 |
| #6 DILUTION | 1/15,625 |
| #7 DILUTION | 1/78,125 |
| #8 DILUTION | 1/390,625 |
| #9 DILUTION | 1/1,953,125 |
| #10 DILUTION | 1/9,765,625 |

It is believed that the various dilutions have the ability to provide an immunotherapeutic response, thereby inducing immune system food tolerance. It should be understood that there could be a homeopathic affect, as well, or in addition to, the immunotherapeutic affect of the procedure of the present application. However, it will be appreciated that with some patients, depending upon their dietary and medical history, this concentration is too strong and may cause temporary exacerbation of food reactions from over-reaction of the immune system. In such cases, the solution may be diluted or otherwise adjusted. Sublingual drops target receptors under the tongue called dendritic cells, which detect molecules in an allergy drop solution and present them to immune system T-cells. These regulatory T-cells are thought to induce and maintain tolerance to antigens. T-cells send a message to the other cells that the food extracts are tolerated, although the exact method is unknown. The T-cells' messages to other cells are sent directly (cell-to-cell) or indirectly (via cytokines made by the other cells). In the preferred embodiment, other common foods in the patient's diet can be administered as food extracts in addition to the extracts in the "super-combo" vial. In an alternative embodiment, soy, another common food allergen, can be administered as a food extract in addition to the extracts in the "super-combo" vial.

Figure 1B:
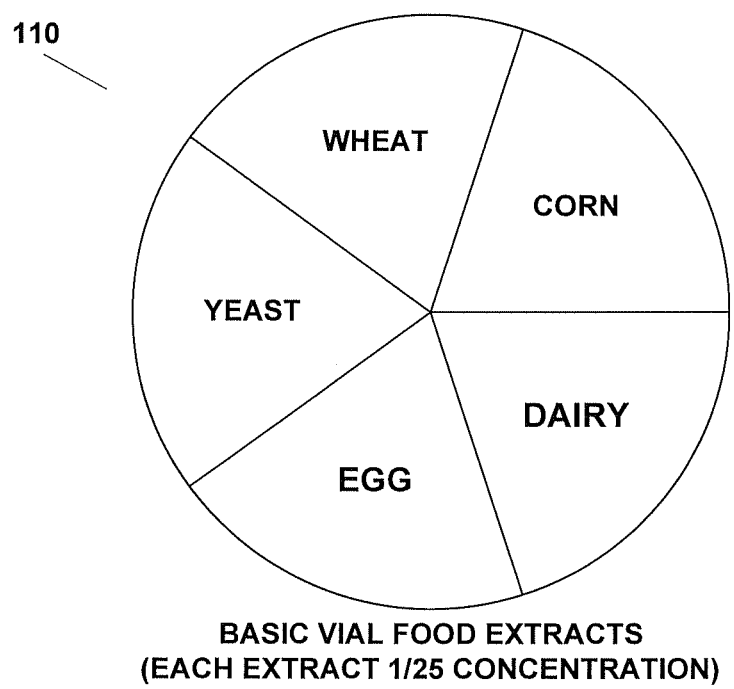
FIG. 1B is a chart showing extracts used in a "basic" vial of solution according to the present application.

Referring now also to FIG. 1B in the drawings, there is shown a chart 110 listing the extracts used in a preferred embodiment of a "basic" vial solution according to the present application. Wheat, corn, dairy, egg, yeast (WCDEY) are believed to be some of the most common foods that cause delayed food allergies (chronic food sensitivity). The WCDEY are administered as food extracts in a water and glycerin solution, disposed within a dropper vial, in a specific dilution. This solution is referred to as a "basic" vial. Other common foods in the patient's diet can be administered as food extracts in addition to the extracts in the "basic" vial. For example, soy can be administered as a food extract in addition to the extracts in the "basic" vial.

Figure 1C:
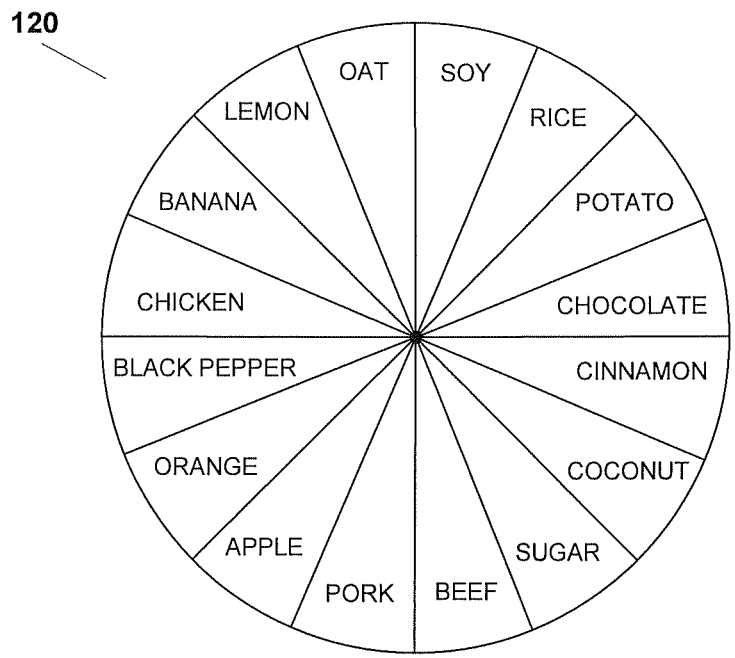
FIG. 1C is a chart showing extracts used in an "ultra-combo" vial of solution according to the present application.

Referring now also to FIG. 1C in the drawings, there is shown a chart 120 listing the extracts used in a preferred embodiment of an "ultra-combo" vial solution according to the present application. Soy, rice, potato, chocolate, cinnamon, coconut, sugar, beef, pork, apple, orange, black pepper, chicken, banana, lemon, and oat are believed to be other common foods that cause delayed food allergies (chronic food sensitivity). The aforementioned food extracts are administered in a water and glycerin solution, disposed within a dropper vial, in a specific dilution. This solution is referred to as an "ultra-combo" vial. Other common foods in the patient's diet can be administered as food extracts in addition to the extracts in the "ultra-combo" vial.

Figure 1D:
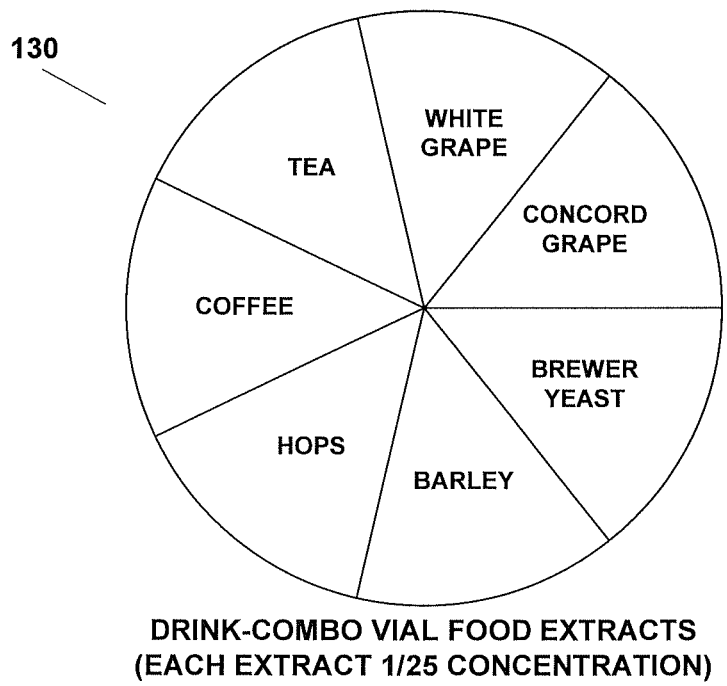
FIG. 1D is a chart showing extracts used in a "drink combo" vial of solution according to the present application.

Referring now also to FIG. 1D in the drawings, there is shown a chart 130 listing the extracts used in a preferred embodiment of a "drink-combo" vial solution according to the present application. Tea, white grape, concord grape, brewer yeast, barley, hops, coffee, and tea are believed to be other common foods that cause delayed food allergies (chronic food sensitivity). The aforementioned food extracts are administered in a water and glycerin solution, disposed within a dropper vial, in a specific dilution. This solution is referred to as a "drink-combo" vial. Other common foods in the patient's diet can be administered as food extracts in addition to the extracts in the "drink-combo" vial.

Figure 1E:
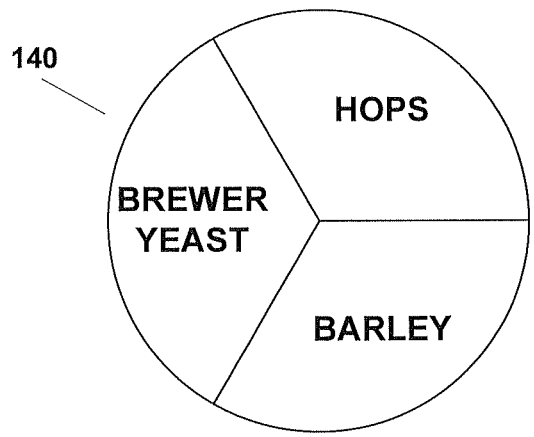
FIG. 1E is a chart showing extracts used in a "beer" vial of solution according to the present application.

Referring now also to FIG. 1E in the drawings, there is shown a chart 140 listing the extracts used in a preferred embodiment of a "beer" vial solution according to the present application. Brewer yeast, barley, and hops are believed to be other common foods that cause delayed food allergies (chronic food sensitivity). The aforementioned food extracts are administered in a water and glycerin solution, disposed within a dropper vial, in a specific dilution. This solution is referred to as a "beer" vial. Other common foods in the patient's diet can be administered as food extracts in addition to the extracts in the "beer" vial.

Figure 1F:
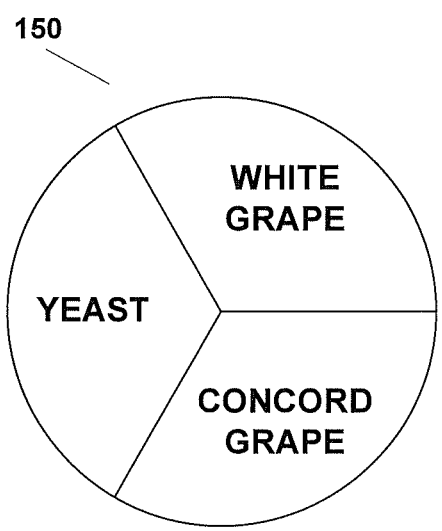
FIG. 1F is a chart showing extracts used in a "wine" vial of solution according to the present application.

Referring now also to FIG. 1F in the drawings, there is shown a chart 150 listing the extracts used in a preferred embodiment of a "wine" vial solution according to the present application. Yeast, white grape, and concord grape are believed to be other common foods that cause delayed food allergies (chronic food sensitivity). The aforementioned food extracts are administered in a water and glycerin solution, disposed within a dropper vial, in a specific dilution. This solution is referred to as a "wine" vial. Other common foods in the patient's diet can be administered as food extracts in addition to the extracts in the "wine" vial.

Figure 1G:
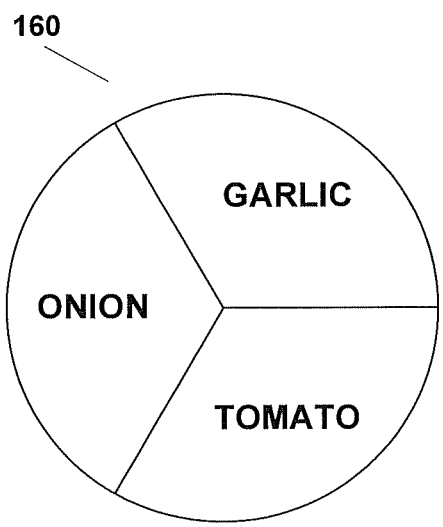
FIG. 1G is a chart showing extracts used in a "GOT" vial of solution according to the present application.

Referring now also to FIG. 1G in the drawings, there is shown a chart 160 listing the extracts used in a preferred embodiment of a "GOT" vial solution according to the present application. Garlic, onion, and tomato are believed to be other common foods that cause delayed food allergies (chronic food sensitivity). The aforementioned food extracts are administered in a water and glycerin solution, disposed within a dropper vial, in a specific dilution. This solution is referred to as a "GOT" vial. Other common foods in the patient's diet can be administered as food extracts in addition to the extracts in the "GOT" vial.

Figure 2A:
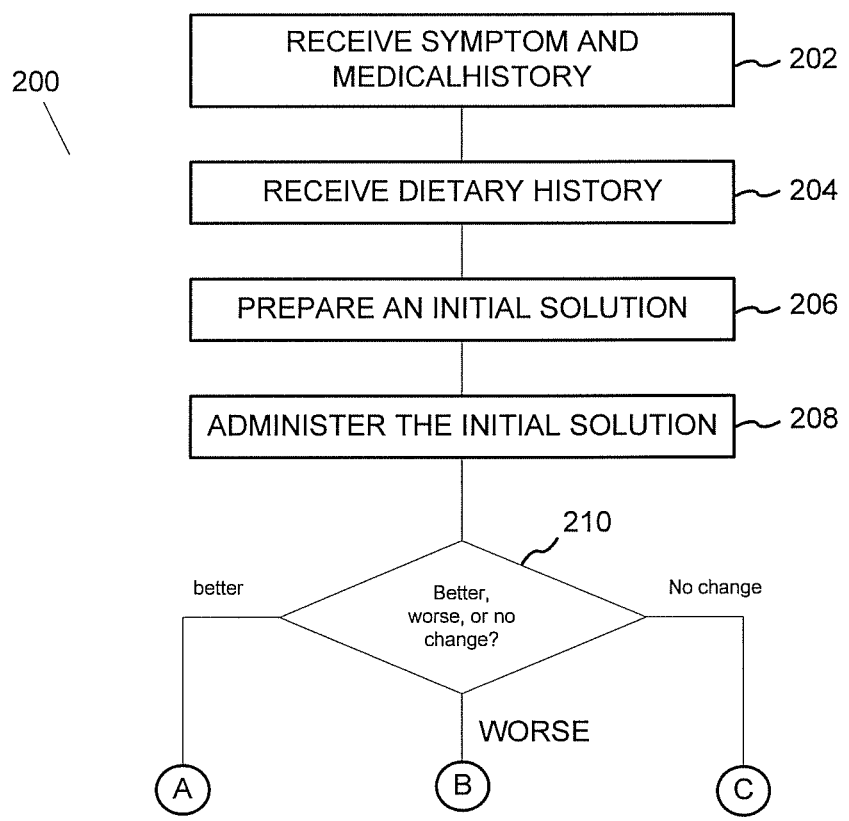
FIG. 2A is a diagram of a method for testing and treating delayed food allergies according to the present application.

Referring now also to FIG. 2A in the drawings, a flowchart 200 depicting the preferred embodiment of a method for testing and treating delayed food allergies according to the present application is shown. Method 200 begins at 202, in which a detailed symptom and medical history of the patient is taken. Chart 1200, shown in FIGS. 12A and 12B, represents a food sensitivity questionnaire for facilitating taking the patient symptom and medical history. Referring now also to FIG. 13 in the drawings, a chart 1300 is a delayed food allergy evaluation guide used in method for testing and treating delayed food allergies disclosed in the present application is illustrated. Chart 1300 is used to facilitate acquiring patient symptom and medical history data. The method then proceeds to 204. At 204, a dietary history of foods common in the patient's diet is taken. In the preferred embodiment, the patient is asked for a list of favorite foods and/or foods frequently consumed in the patient's diet. The taking of these detailed histories is are important steps in the process of the subject application, as the patient's symptoms, and medical and dietary histories, play important roles in the selection of the type, make-up, and extract concentration levels of the initial and subsequent vials that are administered to the patient. The method then proceeds to 206.

At 206, an initial solution is prepared for sublingual administration. In the preferred embodiment, the initial solution is a "super-combo" vial, wherein WCDEYGOT are combined with glycerin and water. In an alternative embodiment, the initial solution is a GOT vial or "basic" vial. The "basic" vial is often the initial solution administered to small children, and the "super-combo" vial is usually the initial solution administered to adults and older children. The method then proceeds to 208.

Figure 16:
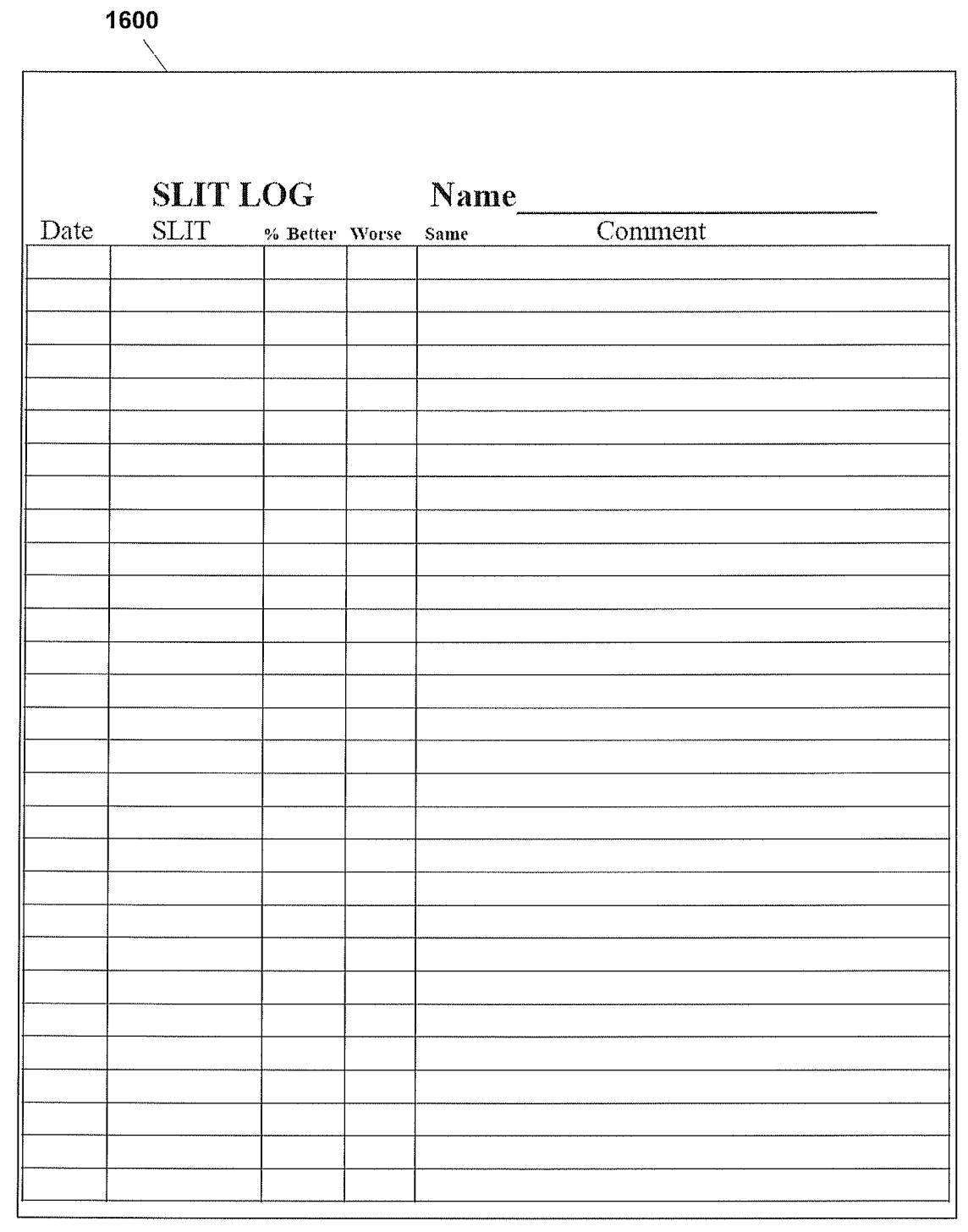

At 208, the solution is administered to the patient over a trial period. In the preferred embodiment, the solution is administered three times daily. For example, a single drop is placed under the tongue first thing in the morning, at midafternoon, and at bedtime, with the best results occurring if the drops are not administered at or during a mealtime. The trial period preferably lasts two weeks. Worsening of the patient's symptoms may occur. In approximately 10% of patients; when this occurs, it routinely will start to occur during the first few days of drop use. The patient is asked to discontinue that drop dilution, and obtain a weaker dilution for another 2 week trial period. If improvement occurs, there will be a gradual decrease in symptoms over several days, then when the drops are stopped after the two week trial period, the original symptoms quickly return during the first few days off the drops. Referring now also to FIG. 14 in the drawings, a chart 1400 is a sublingual food drop guide used in method for testing and treating delayed food allergies disclosed in the present application is illustrated. Chart 1400 is used to facilitate acquiring patient symptom data during the method disclosed in the present application. Referring now also to FIG. 16 in the drawings, a chart 1600 is a SLIT log used in method for testing and treating delayed food allergies disclosed in the present application is illustrated. Chart 1600 is used to facilitate acquiring patient symptom data during the method disclosed in the present application. The method then proceeds to 210.

At 210, it is determined whether the patient's symptoms are improving, getting worse, or experiencing no change. In the preferred embodiment, the patient is brought in to a first follow-up consultation to give an account of the degree of the symptoms as compared with the degree of the symptoms at the initial consultation. If the patient's symptoms have improved since the initial consultation, the method proceeds to 212 (continued in FIG. 2B). If the patient's symptoms have gotten worse since the initial consultation, the method proceeds to 234 (continued in FIG. 2C). If the patient's symptoms experience no change since the initial consultation, the method proceeds to 246 (continued in FIG. 2D).

Figure 2B:
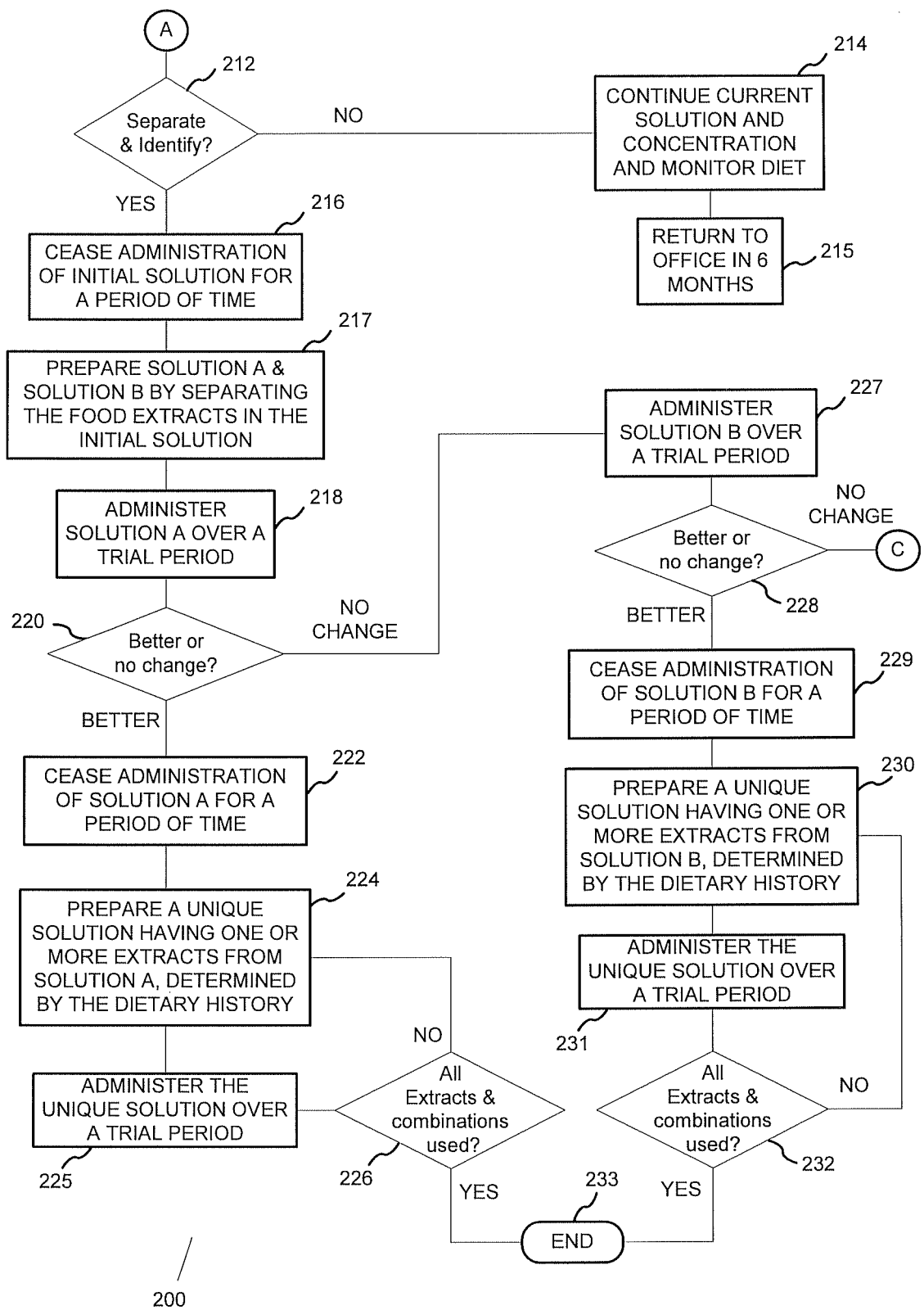
FIG. 2B is a continuation of the diagram of FIG. 2A according to the present application.

Referring now also to FIG. 2B in the drawings, there is shown a continuation of the diagram of FIG. 2A according to the present application. At 212, it is determined whether the food extracts in the initial solution will be separated and the offending extracts further identified. For example, a cost benefit analysis of further testing and treatment may be undertaken. If it is decided that the initial solution will be separated and further identified, the method proceeds to 216. If it is decided that the initial solution will not be separated and further identified, the method proceeds to 214.

At 214, because the patient experienced an improvement in symptoms with the initial solution, the patient continues administration of the current solution at the current concentration, and monitors the diet. The method then proceeds to 215. At 215, the patient returns to the doctor's office in six months for a second follow-up consultation. At 216, administration of the initial solution is ceased for a period of time. In the preferred embodiment, the patient continues eating foods that cause allergy symptoms without administering drops for up to two weeks, or until symptoms return. The method then proceeds to 217.

At 217, solution A and solution B are prepared by separating the food extracts in the initial solution. In the preferred embodiment, a "super-combo" vial was used as the initial solution, and solution A contains WCDEY food extracts, glycerin, and water at a $\frac{1}{25}$ C concentration, and solution B contains GOT food extracts, glycerin, and water at a $\frac{1}{25}$ C concentration. The method then proceeds to 218.

At 218, solution A is administered to the patient over a trial period. In the preferred embodiment, the solution is administered three times daily. A single drop is placed under the tongue first thing in the morning, at mid-afternoon, and at bedtime. The trial period preferably lasts two weeks. The method then proceeds to 220.

At 220, it is determined whether the patient's symptoms are getting better or experience no change. In the preferred embodiment, the patient is brought in for a second follow-up consultation to give an account of the degree of the symptoms as compared with the degree of the symptoms at the first follow-up consultation. If the patient's symptoms have improved since the first follow-up consultation, the method proceeds to 222. If the patient's symptoms experience no change since the first follow-up consultation, the method proceeds to 227.

At 222, administration of solution A is ceased for a period of time. In the preferred embodiment, the patient continues eating foods that cause allergy symptoms without administering drops for up to two weeks, or until symptoms return. The method then proceeds to 224.

At 224, a unique solution is prepared by separating the food extracts in the initial solution. In the preferred embodiment, the unique solution contains one or more WCDEY food extracts, glycerin, and water at a $\frac{1}{25}$ C concentration. The unique solution must have at least one less food extract than solution A, unless other food extracts are added. It is preferred that the food extracts chosen for the unique solution be chosen based on the patient's dietary history. The method then proceeds to 225.

At 225, the unique solution is administered to the patient over a trial period. In the preferred embodiment, the solution is administered three times daily. In a second exemplary embodiment, a single drop is placed under the tongue first thing in the morning, at mid-afternoon, and at bedtime. The trial period preferably lasts two weeks. The method then proceeds to 226.

At 226, it is determined whether all food extracts and combinations thereof have been used. The unique solution must be unique; meaning that the exact same combination of extracts must not have been used in the unique solution for this patient before. If all extracts and combinations thereof have been used in the unique solution for this patient, the method proceeds to 233. If all extracts and combinations thereof have not been used in the unique solution for this patient, the method proceeds to 224.

At 227, solution B is administered to the patient over a trial period. In the preferred embodiment, the solution is administered three times daily. A single drop is placed under the tongue first thing in the morning, at mid-afternoon, and at bedtime. The trial period preferably lasts two weeks. The method then proceeds to 220.

At 228, it is determined whether the patient's symptoms are getting better or experience no change. In the preferred embodiment, the patient is brought in for a third follow-up consultation to give an account of the degree of the symptoms as compared with the degree of the symptoms at the second follow-up consultation. If the patient's symptoms have improved since the second follow-up consultation, the method proceeds to 229. If the patient's symptoms experience no change since the second follow-up consultation, the method proceeds to 246 (continued in FIG. 2C).

At 229, administration of solution B is ceased for a period of time. In the preferred embodiment, the patient continues eating foods that cause delayed allergy symptoms without administering drops for up to two weeks, or until symptoms return. The method then proceeds to 230.

At 230, a unique solution is prepared by separating the food extracts in the initial solution. In the preferred embodiment, the unique solution contains one or more GOT food extracts, glycerin, and water at a $\frac{1}{25}$ C concentration. The unique solution must have at least one less food extract than solution B, unless other food extracts are added. The food extracts chosen for the unique solution are preferably chosen based on the patient's dietary history. The method then proceeds to 231.

At 231, the unique solution is administered to the patient over a trial period. In the preferred embodiment, the solution is administered three times daily. A single drop is placed under the tongue first thing in the morning, at mid-afternoon, and at bedtime. The trial period preferably lasts two weeks. The method then proceeds to 232.

At 232, it is determined whether all food extracts and combinations thereof have been used. The unique solution must be unique; meaning that the exact same combination of extracts must not have been used in the unique solution for this patient before. If all extracts and combinations thereof have been used in the unique solution for this patient, the method proceeds to 233. If all extracts and combinations thereof have not been used in the unique solution for this patient, the method proceeds to 230.

At 233, the method for testing and treating delayed food allergies ends. In the preferred embodiment, the results on the patient's symptoms by the different unique solutions are analyzed and the food allergies are identified. A long-term customized treatment plan, based upon the analysis, is initiated with the patient. Returning visits and evaluations may be prescribed.

It is the intent of the procedure to continue to weaken or strengthen the food extracts until the patient has satisfactory symptom relief without symptom provocation.

Figure 2C:
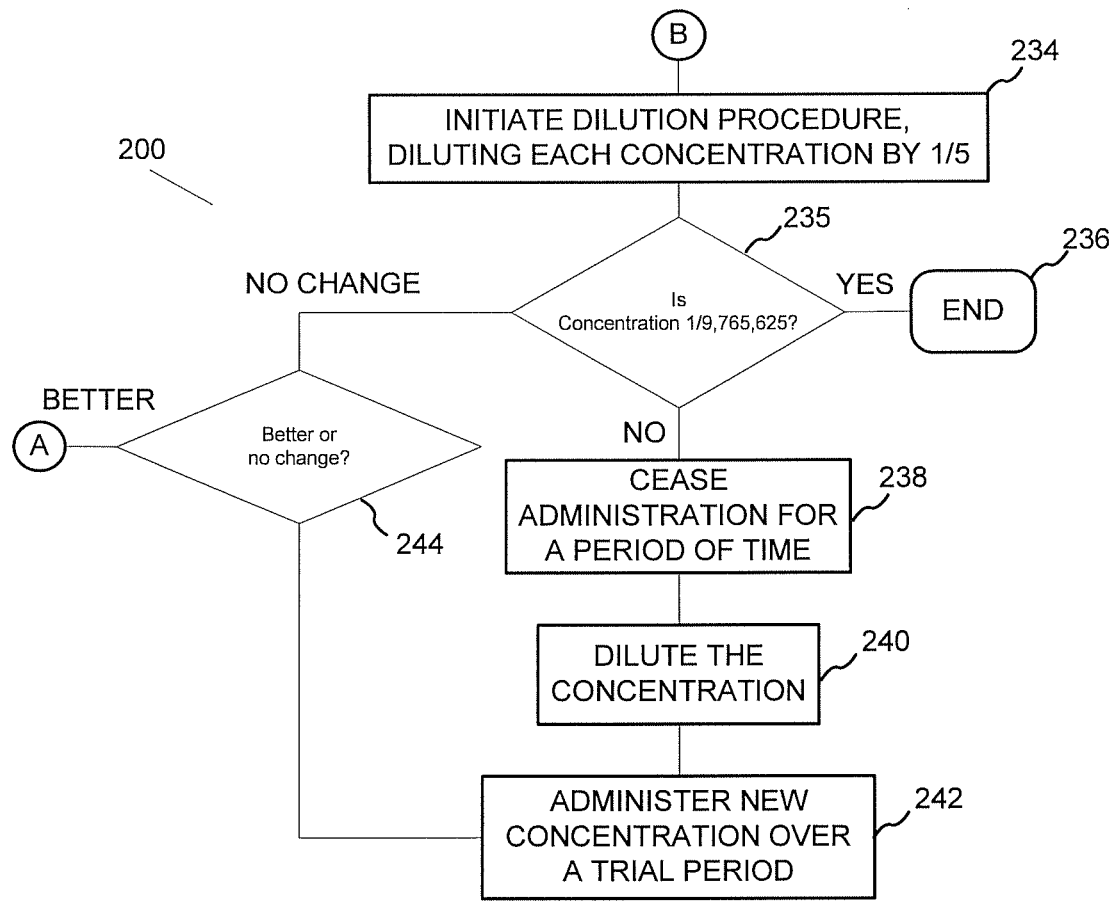
FIG. 2C is a continuation of the diagram of FIG. 2A according to the present application.

Referring now also to FIG. 2C in the drawings, there is shown a continuation of the diagram of FIG. 2A according to the present application. At step 234 a dilution procedure is initiated, with each additional concentration being diluted by $1/5$. At 235, it is determined whether the initial solution concentration has been diluted to $1/9,765,625$ C. In the preferred embodiment, the $1/9,765,625$ C concentration of the initial solution is too low to affect the patient. If the $1/9,765,625$ C concentration has been reached, the method proceeds to 236. If the $1/9,765,625$ C concentration has not been reached, the method proceeds to 238.

At 238, administration of the initial solution is ceased for a period of time. In the preferred embodiment, the patient continues eating foods that cause allergy symptoms without administering drops for up to two weeks, or until symptoms return. The method then proceeds to 240.

At 240, the solution concentration is diluted in order to find a weaker dilution that will be less likely to provoke symptoms. In the preferred embodiment, the initial solution is diluted by combining 1 cc of food extract with 4 cc of a diluent, by volume. The diluent is comprised of 1 part glycerin and 1 part water, by volume. Glycerin is used as a preservative. The diluted solution is preferably diluted to $1/5$ of its parent concentration. The method then proceeds to 242.

At 242, a diluted solution is administered to the patient over a trial period. In the preferred embodiment, the solution is administered three times daily. A single drop is placed under the tongue first thing in the morning, at mid-afternoon, and at bedtime. The trial period preferably lasts two weeks. The method then proceeds to 244.

At 244, it is determined whether the patient's symptoms are getting better or experience no change. In the preferred embodiment, the patient is brought in for a second follow-up consultation to give an account of the degree of the symptoms as compared with the degree of the symptoms at the first follow-up consultation. If the patient's symptoms have improved since the first follow-up consultation, the method proceeds to 212 (continued in FIG. 2B). If the patient's symptoms experience no change since the first follow-up consultation, the method proceeds to 234.

At 236, the method for testing and treating delayed food allergies ends. In the preferred embodiment, the results on the patient's symptoms experience no change, so the patient may try another food mix such as "Ultra-combo" or the patient may want to try a rotation or elimination diet with the patient returning in six months for a follow-up consultation. It should be understood that very weak dilutions may be needed in the very sensitive patient.

Figure 2D:
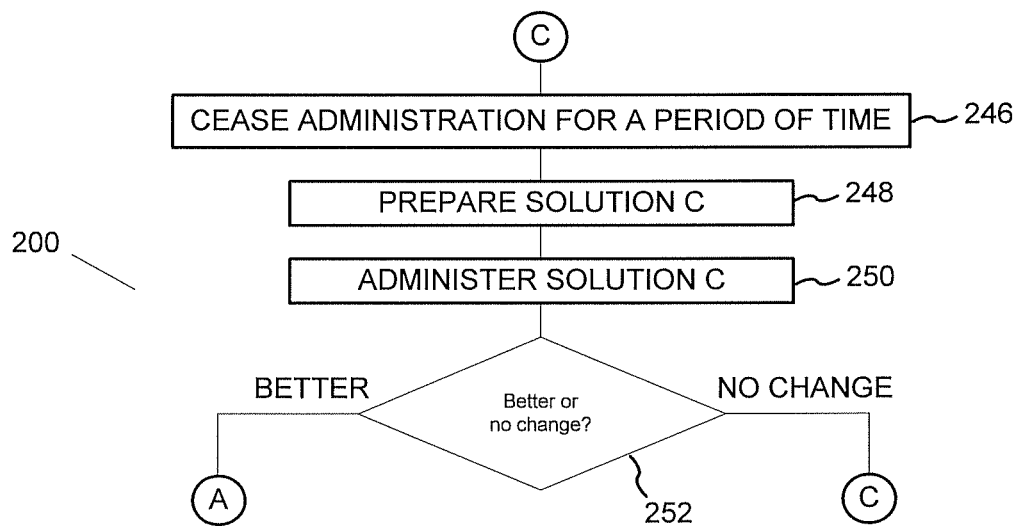
FIG. 2D is a continuation of the diagram of FIG. 2A according to the present application.

Referring now also to FIG. 2D in the drawings, there is shown a continuation of the diagram of FIG. 2A according to the present application. At 246, administration of the initial solution is ceased for a period of time. In the preferred embodiment, the patient continues eating foods that cause allergy symptoms without administering drops for up to two weeks, or until symptoms return. The method then proceeds to 248.

At 248, solution C is prepared by adding food extracts from foods that are common to the patient's diet, as disclosed by the patient's dietary history. In the preferred embodiment, the unique solution contains soy, glycerin, and water at a $1/25$ C concentration. The food extracts chosen for the unique solution are preferably chosen based on the patient's dietary history, especially considering foods frequent in the patient's diet. The method then proceeds to 250.

At 250, solution C is administered to the patient over a trial period. In the preferred embodiment, the solution is administered three times daily. A single drop is placed under the tongue first thing in the morning, at mid-afternoon, and at bedtime. The trial period preferably lasts two weeks. The method then proceeds to 252.

At 252, it is determined whether the patient's symptoms are getting better or experience no change. In the preferred embodiment, the patient is brought in for a second follow-up consultation to give an account of the degree of the symptoms as compared with the degree of the symptoms at the first follow-up consultation. If the patient's symptoms have improved since the first follow-up consultation, the method proceeds to 212. If the patient's symptoms experience no change since the first follow-up consultation, the method can either proceed to 246 or may try another food mix such as "Ultra-combo" or the patient may want to try a rotation or elimination diet with the patient returning in six months for a follow-up consultation.

In a hypothetical case, a patient having delayed food allergies discloses a symptom history detailing the symptoms suffered. Additionally, the patient discloses a dietary history detailing foods common to the patient's diet. A "super-combo" vial is prepared for the patient. The patient administers one sublingual drop three times daily for two weeks. The patient then returns for a first follow-up consultation to provide an update or change in patient symptoms: better, worse or same.

If, after the first follow-up consultation, the patient's symptoms have gotten better, the patient and doctor discuss whether to separate the extracts and further identify the allergen, or to continue the current regimen and monitor the patient's diet for six months, then checkup. If the decision is to separate and identify the extracts in the "super-combo" vial, the extracts are divided into two groups. Group 1 can contain WCDEY, and group 2 can contain GOT. The patient ceases administration of the sublingual drops for as short as three days, but as long as two weeks, after which, the vial containing group 1 extracts is administered to the hypothetical patient for a period of two weeks. The patient then returns for a second follow-up consultation to provide an update or change in patient symptoms: better, worse or same.

If, after the second follow-up consultation, the patient's symptoms have gotten better, the allergen is contained in the group 1 solution and the food extracts contained in the group 1 solution are separated so to further isolate and identify the allergen. A solution containing only one food extract, glycerin, and water is administered to the patient for two weeks, the patient then returns for a follow-up consultation to provide an update or change in patient symptoms: better, worse or same. This process of administration for two weeks followed by a follow-up consultation is repeated with a solution containing one food extract from group one until all the extracts have been individually administered. In this way, the offending food allergen can be isolated and identified, thereby equipping the patient with the knowledge of what foods can cause the patient's allergic reaction.

Figure 3:
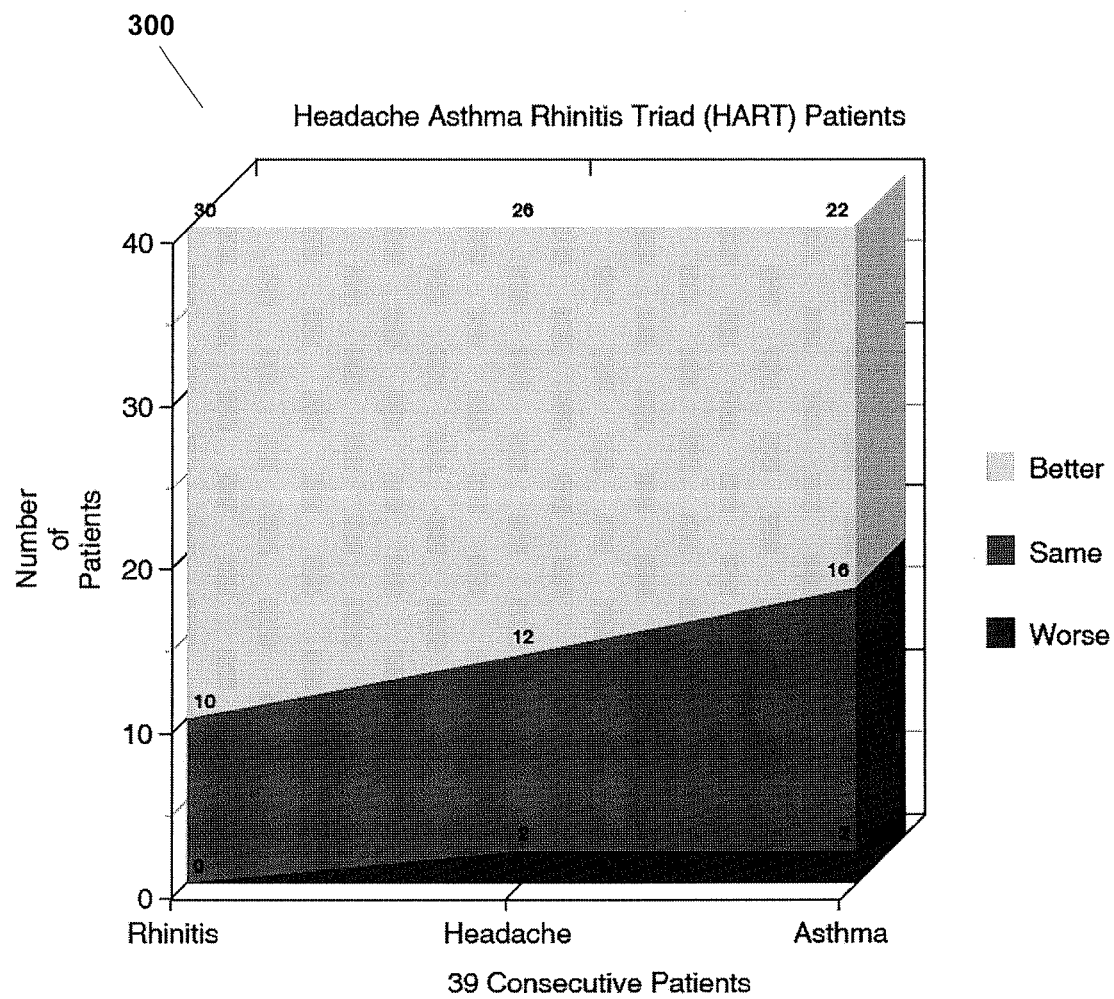
FIG. 3 is a chart showing responses of patients with HART (headache, asthma, and rhinitis triad) symptoms to the method for testing and treating delayed food allergies disclosed in the present application.

Referring now also to FIG. 3 in the drawings, a chart 300 detailing patient responses to the method for testing and treating delayed food allergies disclosed in the present application is illustrated. Data from 39 consecutive patients, with follow up, with headache, asthma, and rhinitis triad (HART) symptoms is represented in chart 300.

Figure 4:
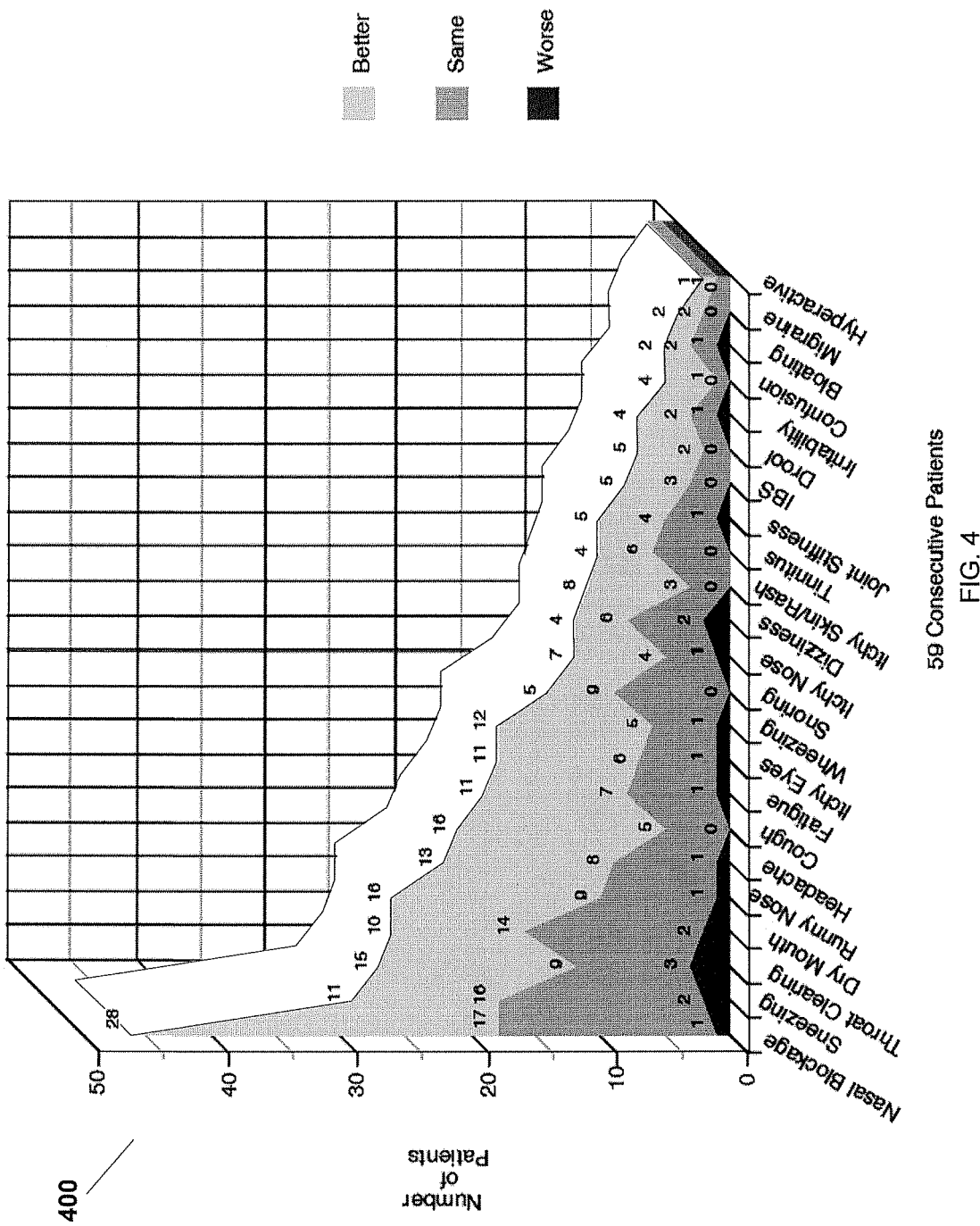
FIG. 4 is a chart showing responses of patients with various symptoms to the method for testing and treating delayed food allergies disclosed in the present application.

Referring now also to FIG. 4 in the drawings, a chart 400 detailing patient responses to the method for testing and treating delayed food allergies disclosed in the present application is illustrated. Data from 59 consecutive patients with various symptoms is represented in chart 400. For example, after taking the sublingual drops of the patients experiencing nasal blockage, 28 patients experienced improvement, 17 patients experienced no change, and 1 patient experienced a worsening of the nasal blockage. Chart 400 also reveals that of the patients experiencing snoring symptoms, 5 patients experienced improvement, 9 experienced no change, and 0 patients experienced a worsening of the symptom, after taking the sublingual drops.

Figure 5:
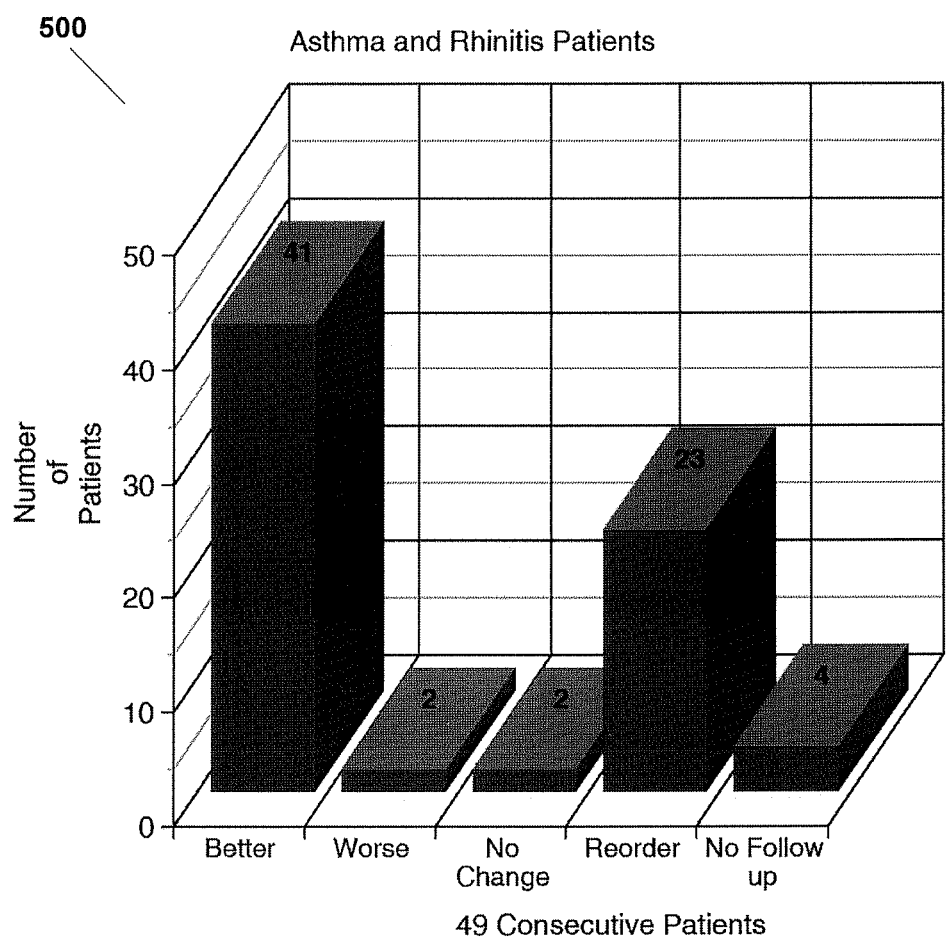
FIG. 5 is a chart showing responses of patients with asthma and rhinitis symptoms to the method for testing and treating delayed food allergies disclosed in the present application.

Referring now also to FIG. 5 in the drawings, a chart 500 detailing patient responses to the method for testing and treating delayed food allergies disclosed in the present application is illustrated. Data from 49 consecutive patients with asthma and rhinitis symptoms is represented in chart 500. Following an administration of sublingual drops to 49 patients, 41 of the patients experienced an improvement in their symptoms, 2 experienced a worsening of symptoms, 2 experienced no change in their symptoms, and 4 without follow up. In addition, 23 patients reordered the sublingual drops. Chart 500 represents 49 actual patients that were experiencing asthma and rhinitis symptoms prior to receiving sublingual drops according to the present application.

Figure 6:
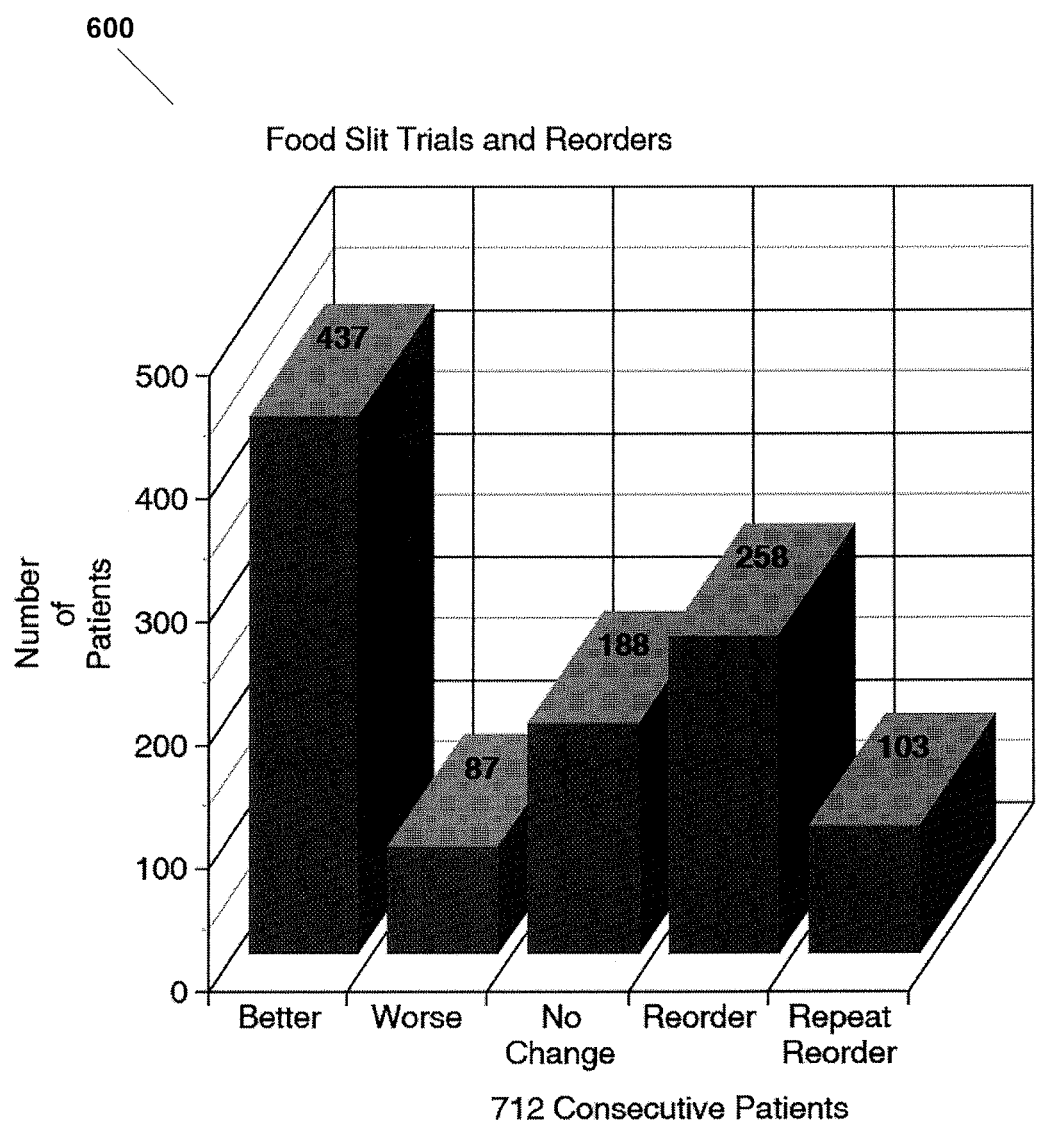
FIG. 6 is a chart showing responses of patients to the method for testing and treating delayed food allergies disclosed in the present application.

Referring now also to FIG. 6 in the drawings, a chart 600 detailing patient responses to the method for testing and treating delayed food allergies disclosed in the present application is illustrated. Data from 712 consecutive patients, with follow up, having sublingual drops according to the method of the present application is represented in chart 600. Following an administration of sublingual drops to 712 patients, 437 of the patients experienced an improvement in their symptoms, 87 experienced a worsening of symptoms, and 188 experienced no change in their symptoms. In addition, 258 patients reordered the sublingual drops and 103 patients reordered the sublingual drops again. Chart 600 represents 712 actual patients that received sublingual drops according to the method of the present application.

Figure 7:
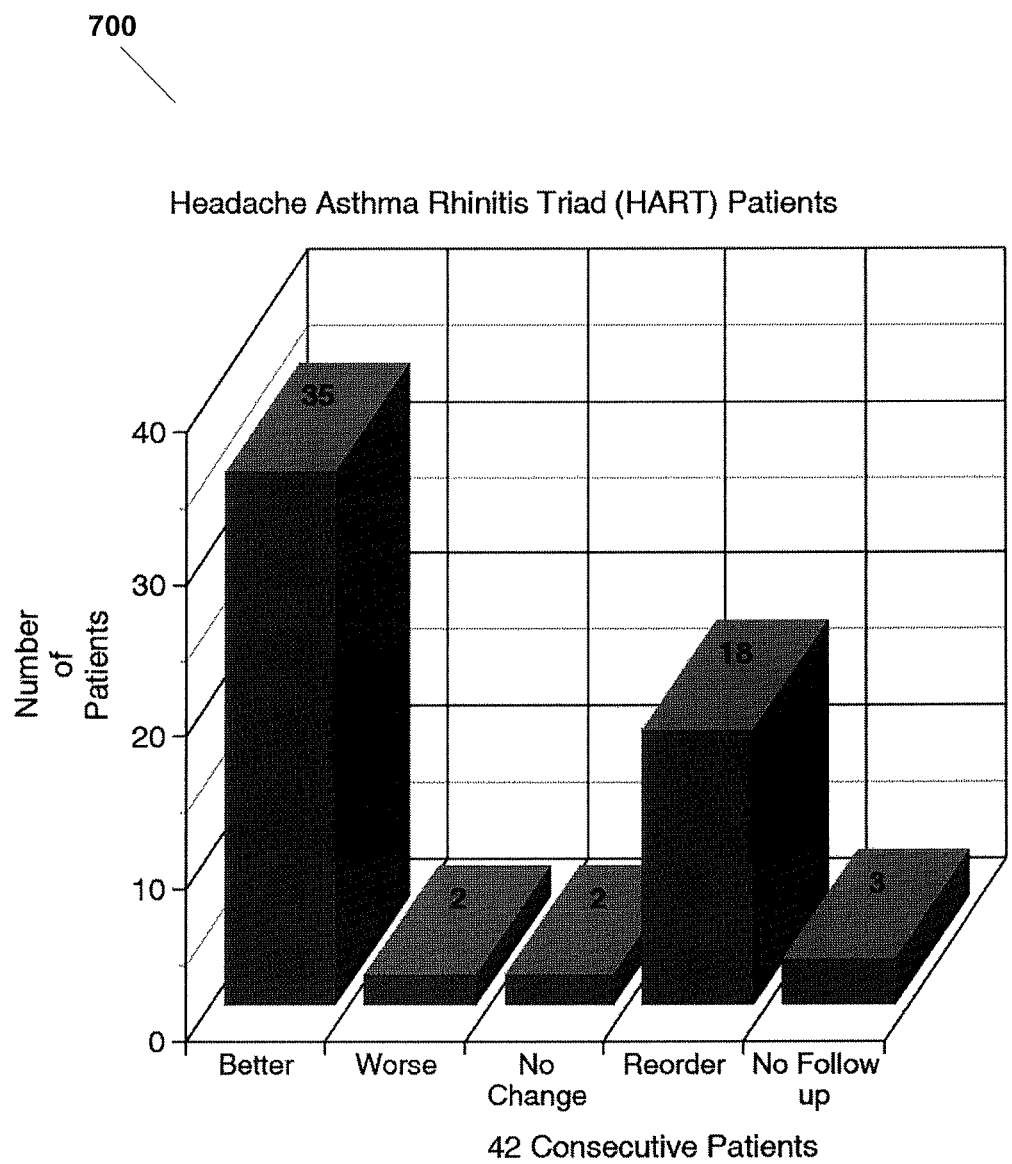
FIG. 7 is a chart showing responses of patients with HART (headache, asthma, and rhinitis triad) symptoms to the method for testing and treating delayed food allergies disclosed in the present application.

Referring now also to FIG. 7 in the drawings, a chart 700 detailing patient responses to the method for testing and treating delayed food allergies disclosed in the present application is illustrated. Data from 42 consecutive patients with headache, asthma, and rhinitis triad (HART) symptoms is represented in chart 700. Following an administration of sublingual drops to 42 patients, 35 of the patients experienced an improvement in their symptoms, 2 experienced a worsening of symptoms, 2 experienced no change in their symptoms, and 3 patients did not follow up. In addition, 18 patients reordered the sublingual drops. Chart 700 represents 42 actual patients that were experiencing headache, asthma, and rhinitis triad (HART) symptoms prior to receiving sublingual drops according to the present application.

Figure 8A:
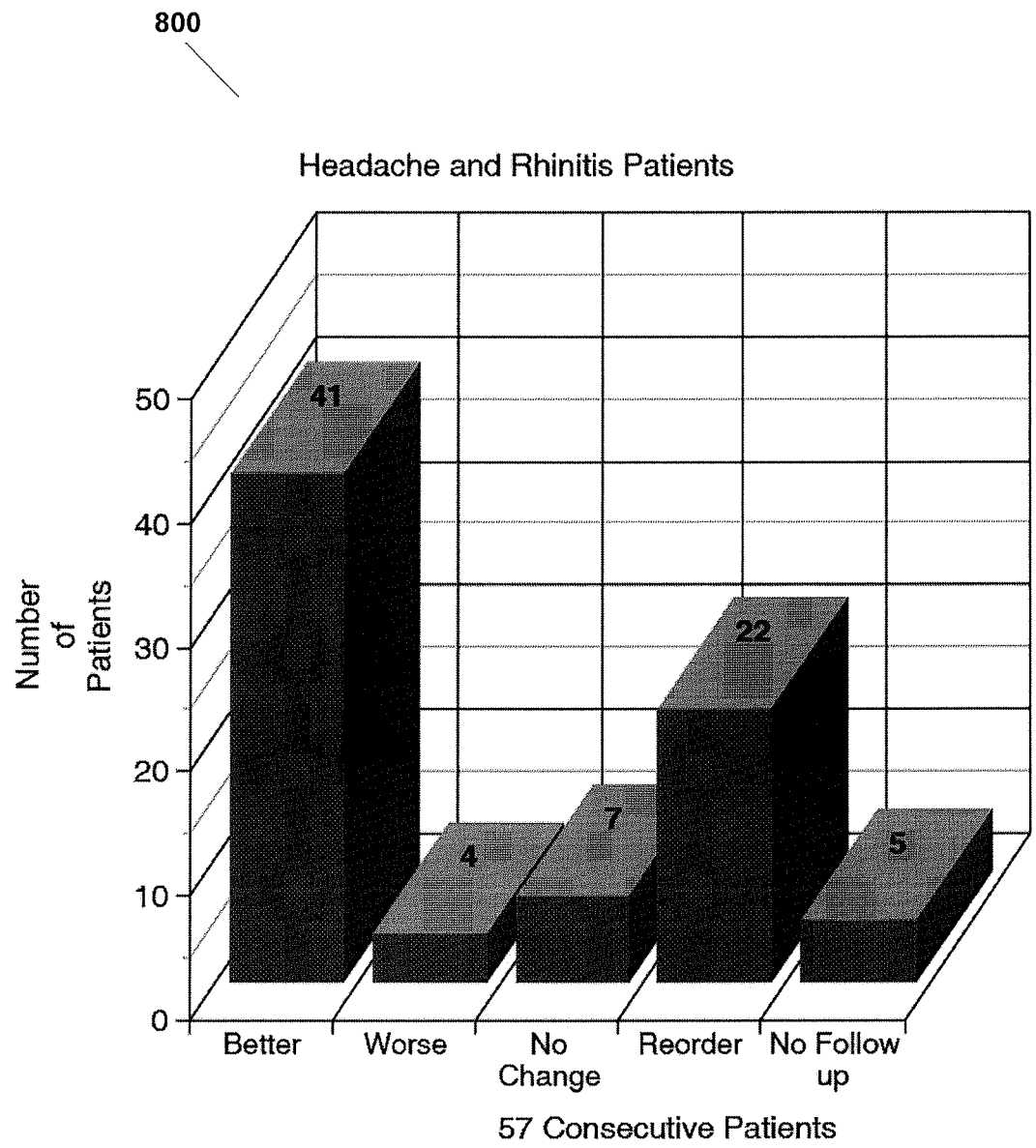
FIG. 8A is a chart showing responses of patients with headache and rhinitis symptoms to the method for testing and treating delayed food allergies disclosed in the present application.

Referring now also to FIG. 8A in the drawings, a chart 800 detailing patient responses to the method for testing and treating delayed food allergies disclosed in the present application is illustrated. Data from 57 consecutive patients with headache and rhinitis symptoms is represented in chart 800. Following an administration of sublingual drops to 57 patients, 41 of the patients experienced an improvement in their symptoms, 4 experienced a worsening of symptoms, 7 experienced no change in their symptoms, and 5 patients did not follow up. In addition, 22 patients reordered the sublingual drops. Chart 800 represents 57 actual patients that were experiencing headache and rhinitis symptoms prior to receiving sublingual drops according to the present application.

Figure 8B:
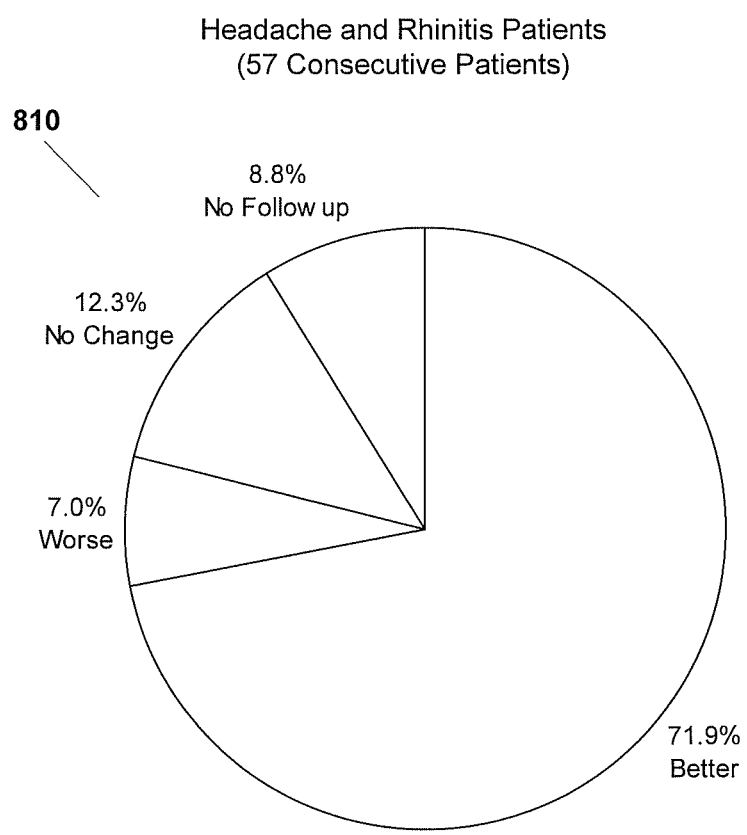
FIG. 8B is a chart showing responses of patients with headache and rhinitis symptoms to the method for testing and treating delayed food allergies disclosed in the present application.

Referring now also to FIG. 8B in the drawings, a chart 810 detailing patient responses to the method for testing and treating delayed food allergies disclosed in the present application is illustrated. Of 57 patients experiencing headache and rhinitis symptoms, 71.9% of the patients expressed an improvement in their symptoms, 7% expressed a worsening of symptoms, and 12.3% expressed no change in their symptoms. Additionally, 8.8% of the patients did not follow up.

Figure 9:
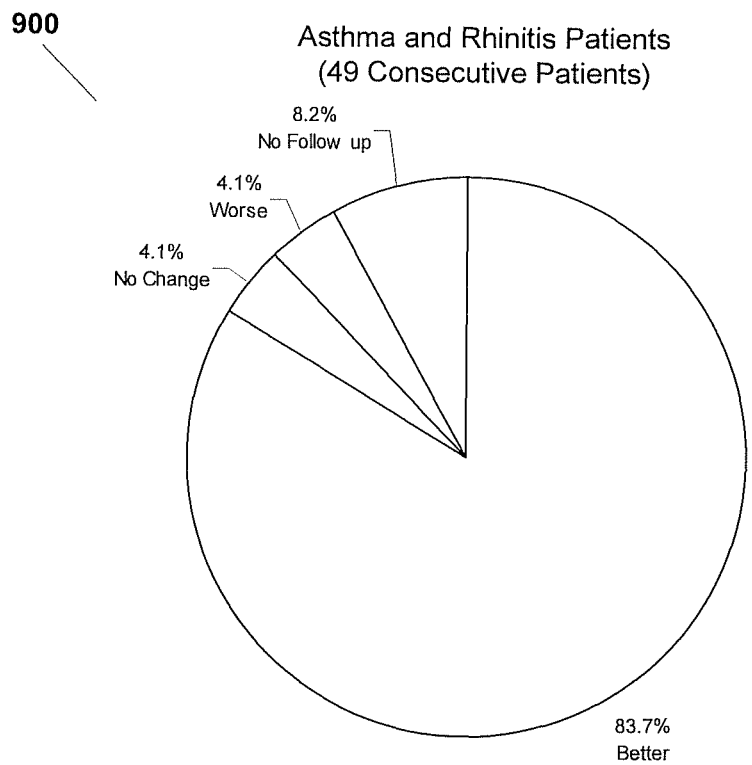
FIG. 9 is a chart showing responses of patients with asthma and rhinitis symptoms to the method for testing and treating delayed food allergies disclosed in the present application.

Referring now also to FIG. 9 in the drawings, a chart 900 detailing patient responses to the method for testing and treating delayed food allergies disclosed in the present application is illustrated. Of 49 patients experiencing asthma and rhinitis symptoms, 83.7% of the patients expressed an improvement in their symptoms, 4.1% expressed a worsening of symptoms, and 4.1% expressed no change in their symptoms. Additionally, 8.2% of the patients did not follow up.

Figure 10A:
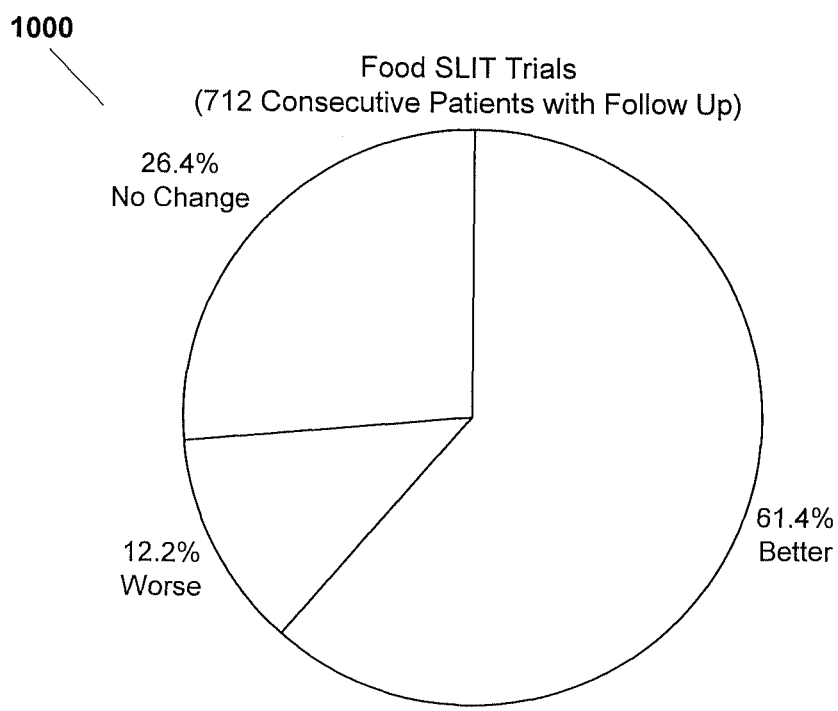
FIG. 10A is a chart showing responses of patients to the method for testing and treating delayed food allergies disclosed in the present application.

Referring now also to FIG. 10A in the drawings, a chart 1000 detailing patient responses to the method for testing and treating delayed food allergies disclosed in the present application is illustrated. Following an administration of sublingual drops to 712 patients, 61.4% of the patients expressed an improvement in their symptoms, 12.2% expressed a worsening of symptoms, and 26.4% expressed no change in their symptoms. Thus, 73.6% of patients experienced a positive response, i.e., improving or worsening of symptoms, to the sublingual drops. The 26.4% of patients that experienced no change in their symptoms either transitioned to an elimination or rotation diet, or chose to have limited further follow-up. Chart 1000 represents actual patients that have responded to follow-up inquiries; i.e., provided an update or change in patient symptoms: better, worse or same.

Figure 10B:
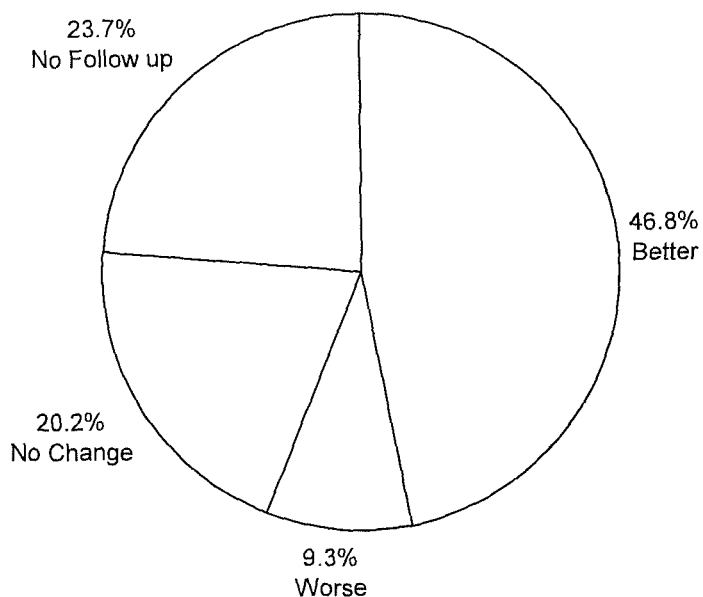
FIG. 10B is a chart showing responses of patients with headache and rhinitis symptoms to the method for testing and treating delayed food allergies disclosed in the present application.

Referring now also to FIG. 10B in the drawings, a chart 1010 detailing patient responses to the method for testing and treating delayed food allergies disclosed in the present application is illustrated. Following an administration of sublingual drops to 933 patients, 46.8% of the patients expressed an improvement in their symptoms, 9.3% expressed a worsening of symptoms, and 20.2% expressed no change in their symptoms. Additionally, 23.7% of the patients did not follow up.

Figure 11:
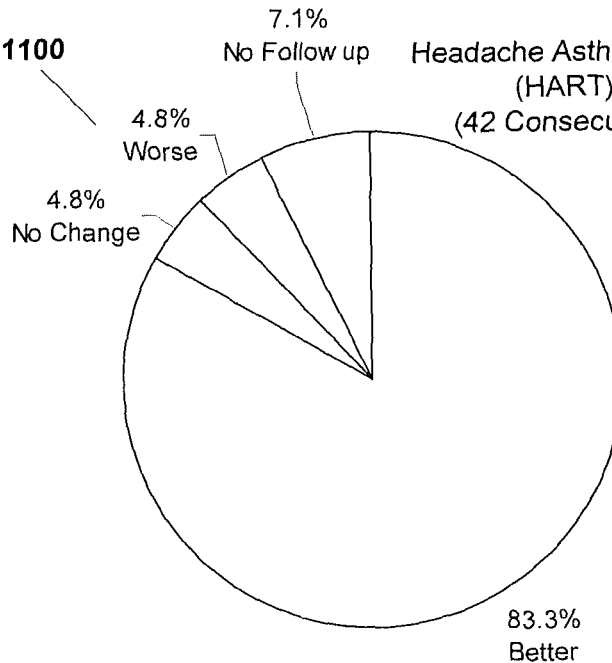
FIG. 11 is a chart showing responses of patients with HART (headache, asthma, and rhinitis triad) symptoms to the method for testing and treating delayed food allergies disclosed in the present application.

Referring now also to FIG. 11 in the drawings, a chart 1100 detailing patient responses to the method for testing and treating delayed food allergies disclosed in the present application is illustrated. Following an administration of sublingual drops to 933 patients experiencing headache, asthma, and rhinitis triad (HART) symptoms, 83.3% of the patients expressed an improvement in their symptoms, 4.8% expressed a worsening of symptoms, and 4.8% expressed no change in their symptoms. Additionally, 7.1% of the patients did not follow up.

As set forth above, the taking of detailed symptom, medical, and dietary histories is important to the procedure of the subject application. In the preferred embodiment, a guide is provided to assist a health care provider in taking a patient's symptom history. In the preferred embodiment, the guide form takes the form of a point system in which a selected point value is assigned to selected symptoms. The results from the guide form can be used to evaluate the patient and select an appropriate initial vial and subsequent vials.

The following table represents an exemplary point system for use in evaluating symptoms of delayed food allergies:

| Guide Form for Evaluating Delayed Food Allergy Symptoms | |
| --- | --- |
| Symptom | Point Value |
| Nasal blockage that is more severe when trying to sleep without the head elevated, that alternates from side to side, with the "down side" more blocked, causing a dry mouth; water is often kept at the bedside; drool spots on the pillow are common | 100 points |
| Itching of the inner corner of the eye, the throat, or deep in the ear | 50 Points |
| Repeated sneezing, several times in a row | 50 Points |
| Craving certain foods or drinks, such as milk, cheese, chocolate, coffee, soft drinks, etc. | 50 Points |
| Chronic sinus/middle ear infections | 50 Points |
| History of nasal polyps or prior sinus surgery | 50 Points |
| Chronic drippy nose, wiping the nose often | 50 Points |
| Chronic headache/migraine | 50 Points |
| Repeated throat clearing | 50 Points |
| Chronic cough | 50 Points |
| Asthma with exercise | 50 Points |
| Snoring that is bothersome at times | 25 Points |
| Dark circles under the eyes | 25 Points |
| Skin itching/hives | 25 Points |
| Fatigue episodes | 25 Points |
| Total: | |

With the foregoing table, the points are added together for each symptom that the patient is experiencing all year, indoors and outdoors. In this exemplary guide form, a delayed food allergy reaction is suggested by a total point value of 100 or more, a total point value of 200 or more suggests a moderate problem, and a total point value of 300 or more suggests a severe problem. It will be appreciated that the foregoing guide form is merely an example of a worksheet-type tool for recording and evaluating delayed food allergy symptoms, and that alternative guide forms having more or fewer symptoms and point values may be used.

The following are several examples of the use of the therapy of the subject application on actual patients:

Example 1

Improved (Partial); 37-Year Old Female

Presented on 11 Mar. 2008 with nasal congestion. Had nasal polypectomy in 1987 and 1989. Has continued to have sinus infections, treated about twice a year for 20 years. These infections cause fatigue, pain in the right cheek and brow areas, and worsening of nasal blockage. Claritin, Zyrtec, Benadryl (antihistamines) produce little relief. Tomato products induce reflux symptoms. Has perennial rhinitis symptoms typical for delayed food sensitivities: repeated sneezing (up to 20 times in a row), and chronic mouth breathing. Inhalant allergy screen with intracutaneous tests showed mild to moderate reaction to mixes of: weed, tree, mold, mite; negative response to grass and animal danders.

Received #2 "super-combo" food sublingual immunotherapy (SLIT) and "not sure if any better," perhaps because of overlying sinusitis, but "felt better" regarding less fatigue, less nasal congestion, and reduced repeated sneezing.

Received sinus endoscopic surgery with adenoidectomy on 29 Apr. 2008.

Postoperatively, on 8 May 2008, she reported that she had found by rotating her diet that beans, taco, corn, chocolate caused eye itching; she has since been limiting these in the diet, but not excluding them. Exam showed half of nasal airway was blocked with edema, even with use of #2 "super-combo" SLIT. Further history was obtained, that she had been drinking soy shakes at least daily, for 2 years. So she was placed on a separate vial of Soy #3 dilution, while still on the #2 "super-combo".

A few days later, she reported that the addition of the #3 Soy caused significant increase of nasal congestion. So she was given a vial of Soy #5 dilution, with clearing of nasal congestion within a week.

Soy #5 was added to "super-combo" #2 SLIT, with continued resolution of nasal congestion.

PLAN: continue Soy #5 added to "super-combo" #2 SLIT, and monitor diet (rotate/eliminate as needed).

Example 2

Improved; 74-Year Old Female

Presented on 7 Jan. 2002 with nearly life-long sinusitis, nasal polyps, multiple sinus procedures, eventually developed fungal sinusitis, referred by a rhinologist, for chronic management. Had typical symptoms of perennial rhinitis symptoms from delayed food sensitivities: nocturnal dependent alternating nasal blockage, repeated sneezing spells, inner corner of eye itching. Developed recurrence of fungal sinusitis in March 2008. Because of severe polypoid edema and the copious fungal mucin, which could not be adequately removed in the clinic, she was scheduled for a surgical procedure to clear the sinuses. She was placed on #2 "super-combo" food SLIT on 8 Apr. 2008. In surgery, on 16 Apr. 2008, there was found no evidence of any fungal mucin and no edema of the sinuses or nasal cavities. NONE.

She reported that she had "enormous relief" within the first two weeks of using the drops: (% relief—symptom) 50%—fatigue; 60%—alternating nasal blockage; 85%—repeated sneezing; 90%—runny nose; 75%—throat clearing; 98%—skin itching; 75%—cough. Still waking with some dry mouth, but thinks related to medications.

PLAN: continue "super-combo" food SLIT at #2 dilution, and monitor diet (rotate/eliminate as needed).

Addendum: friend gave her a 5# bag of Vidalia onions. She had onions several times a day for several days, and experienced moderate return of rhinitis, especially runny nose. She eliminated onion, and in a few days, symptoms were relieved, using SLIT.

PLAN: limit onions, continue SLIT, monitor diet (rotate/eliminate as needed).

Example 3

Worse; 33-Year Old Male

Presented on 2 Apr. 2008 with nasal blockage worsening for several months, awakening with shortness of breath from intense nasal blockage. Occasionally will sneeze a couple times in a row. Exam showed geographic tongue and nasal mucosal edema. Received "super-combo" food SLIT at the standard #2 dilution.

Seen 18 Jun. 2008, and noted snoring worsened on the drops, the nose was more open a week after stopping the drops. Given #3 dilution of "super-combo" food SLIT.

Seen 1 Jul. 2008, and reports no more snoring, nasal blockage 80% better.

PLAN: continue "super-combo" food SLIT at the #3 dilution three times a day, and monitor diet and relate to any worsening of nasal blockage, and to any return of snoring (wife will monitor).

Example 4

No Change; 45-Year Old Male

Presented 17 Apr. 2008 with nasal congestion worsening 6 weeks, worsening when trying to sleep supine. Exam showed very severe septal deviation to the left, resulting in no airway on that side. Right nasal airway was hyperpatent. Received two week trial vial of "super-combo" food SLIT.

On 5 May 2008, reported no change in symptoms with SLIT. Suggested try off tea and diet drinks, which he has had regularly.

Seen 27 May 2008 with nasal blockage persistent. Inhalant allergies evaluated, mildly positive.

PLAN: continue monitoring diet changes and related nasal blockage. Consider nasal surgery for deviated septum. Consider trial vial with Soy, other foods.

It should be understood that the solutions, concentrations, extracts, and make-up, of the vials, trial periods, and procedures set forth herein may be changed, altered, and modified, while remaining within the scope of this application. In addition, although the present application has been described in terms of liquid sublingual drops, it should be understood that the therapy and procedures of the present application may also be conducted with both liquid and solid forms of delivery, including drops, sprays, capsules, tablets, powders, flakes, quick-dissolving strips, and any other suitable form of sublingual administration.

Although the methods of the subject application are particularly well suited for the testing, treatment, and prevention of Gell and Coombs Type IV reactions, it will be appreciated that the systems and methods of the present application may also be used to test, treat, and prevent Gell and Coombs Type I, II, and III reactions. Moreover, it is believed that administration of sublingual drops according to the present application may prevent the allergic march from childhood allergic skin disorders, such as eczema, into asthma and other allergic diseases. For example, the applicant has conducted an in-house retrospective study and found that all children with exercise-induced asthma who were treated with the therapy and procedure of the present application, no longer require the use of pulmonary inhalers. In addition, all children with chronic headaches who were treated with the therapy and procedure of the present application no longer suffer from headaches and no longer require pain medication. Furthermore, ⅔ of adults with asthma who were treated with the therapy and procedure of the present application no longer require the use of an inhaler. All children, and ⅔ of adults with "HART" or Headache Asthma Rhinitis Triad have experienced nearly complete resolution of symptoms while using food SLIT, with marked reduction in need for expensive medications which only offer partial temporary relief. These medications are known to commonly produce undesirable side effects.

Referring now also to FIG. 15 in the drawings, a chart 1500 detailing an overview of sublingual management strategies for food sensitivities (delayed food allergy) is shown. Chart 1500 is meant to provide an overview or guide to a practitioner so as to better understand the method as disclosed in the present application.

It is evident by the foregoing description that the invention of the subject application has significant benefits and advantages, in particular: (1) the initial test is a multi-food test, and not single-food test; (2) there is no need to keep the patient in the clinic a day or more to test a handful of foods; instead, the patient takes the first drop in the office, or at home, and continues the drops, three times a day, at home, work etc., looking for symptoms to change; (3) after the two week trial, the patient completes a symptom questionnaire, and informs the office whether their symptoms are better, worse, or have no change; (4) the process manipulates the combination and concentration of allergens; (5) the patient enjoys the ability to undergo testing and treatment as well as potential prevention of allergy symptoms, while continuing to eat the foods to which they may have a delayed allergy. Commonly, after the patient becomes aware that foods are causing symptoms, and learning what those symptoms are, the patient learns to reduce these food culprits in the diet to avoid "breakthrough" symptoms from overeating the culpable food.

The particular embodiments of the present application disclosed may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the present application. Accordingly, the protection sought herein is as set forth in the claims below. It is apparent that an application with significant advantages has been described and illustrated. Although the present application is shown in a limited number of forms, it is not limited to just these forms, but is amenable to various changes and modifications without departing from the spirit thereof.

The invention claimed is:

1. A method for testing delayed food allergies in a patient, comprising:
   receiving symptom, medical, and dietary histories from the patient, wherein the patient is age 2 to 109;
   assigning a first number according to the patient's age, assigning a second number based on the patient's asthma symptoms, assigning a third number based on the patient's headache symptoms and assigning a fourth number based on the patient's rhinitis symptoms;
   adding said first, second, third and fourth numbers together to determine a sum;
   selecting a first concentration of first food extract and sublingually administering said first concentration of first food extract to said patient;
   wherein the assigning a first number according to the patient's age consists of assigning:
   a number 2 if the patient is 2-29 years old,
   a number 3 if the patient is 30-39 years old,
   a number 4 if the patient is 40-49 years old,
   a number 5 if the patient is 50-59 years old,
   a number 6 if the patient is 60-69 years old,
   a number 7 if the patient is 70-79 years old,
   a number 8 if the patient is 80-89 years old,
   a number 9 if the patient is 90-99 years old and
   a number 10 if the patient is 100-109 years old;
   wherein assigning said second, third and fourth number consists of assigning, for each of asthma, headache and rhinitis respectively, a zero if the symptom is mild, a number 1 if the symptom is moderate and a number 2 if the symptom is severe;
   and, when the sum of the four numbers is:
   2, the first concentration selected is a $\frac{1}{25}$ dilution of the first food extract;
   3, the first concentration selected is a $\frac{1}{125}$ dilution of the first food extract;
   4, the first concentration selected is a $\frac{1}{625}$ dilution of the first food extract;

5, the first concentration selected is a 1/3,125 dilution of the first food extract;
6, the first concentration selected is a 1/15,625 dilution of the first food extract;
7, the first concentration selected is a 1/78,125 dilution of the first food extract;
8, the first concentration selected is a 1/390,625 dilution of the first food extract;
9, the first concentration selected is a 1/1,953,125 dilution of the first food extract;
10, the first concentration selected is a 1/9,765,625 dilution of the first food extract;
11, the first concentration selected is a 1/48,828,125 dilution of the first food extract;
12, the first concentration selected is a 1/244,140,625 dilution of the first food extract;
13, the first concentration selected is a 1/1,220,703,125 dilution of the first food extract;
14, the first concentration selected is a 1/6,103,515,625 dilution of the first food extract;
15, the first concentration selected is a 1/30,517,578,125 dilution of the first food extract;
16, the first concentration selected is a 1/152,587,890,625 dilution of the first food extract;
wherein said 1/25 dilution is the most concentrated food extract and wherein the first food extract comprises a combination of extracts from different foods; and
wherein after administering said concentration of first food extract to said patient, evaluating, after a time, whether the patient's rhinitis, headache and asthma symptoms have improved, worsened or have not changed since said administering of said first concentration of first food extracts.

2. The method of claim 1, wherein if, after said evaluating, the patient's rhinitis, headache or asthma symptoms have not changed, the patient is further sublingually administered a second concentration of said first food extract; wherein said second concentration has a greater concentration than the first concentration of first food extract.

3. The method of claim 1, wherein if, after said evaluating, the patient's rhinitis, headache or asthma symptoms have worsened, the patient is further sublingually administered a second concentration of first food extract; wherein said second concentration has a lower concentration than the first concentration of first food extract.

4. The method of claim 1, wherein if, after said evaluating, the patient's rhinitis, headache or asthma symptoms have improved, sublingual administration of said first concentration of first food extract is continued.

5. The method of claim 1, further comprising:
formulating and sublingually administering a second food extract to said patient;
wherein said second food extract contains at least one type of food extract that was not present in the first food extract.

6. The method of claim 1, wherein:
said first food extract comprises more than one type of food extract and wherein the method further comprises:
formulating and administering a second food extract to said patient; wherein said second food extract excludes at least one food extract that was present in the first food extract.

7. The method of claim 1, wherein the first food extract comprises extracts of wheat, corn, dairy, egg, yeast, garlic, onion and tomato.

8. The method of claim 1, wherein the first food extract comprises extracts of garlic, onion and tomato.

9. The method of claim 1, wherein the first food extract is a combination of two or more food extracts selected from the group consisting of: tomato, onion, garlic, wheat, dairy, corn, yeast, egg, lemon, oat, soy, rice, potato, chocolate, cinnamon, coconut, sugar, beef, pork, apple, orange, black pepper, chicken, banana, tea, white grape, concord grape, barley, hops and coffee.

10. The method of claim 9, wherein said yeast is brewer's yeast.

11. The method of claim 1, wherein said first food extract is a combination of the following extracts: lemon, oat, soy, rice, potato, chocolate, cinnamon, coconut, sugar, beef, pork, apple, orange, black pepper, chicken and banana.

12. The method of claim 1, wherein said first food extract is a combination of the following extracts: tea, white grape, concord grape, barley, hops and coffee.

13. The method of claim 1, wherein said first food extract is a combination of the following extracts: brewer's yeast, hops and barley.

14. The method of claim 1, wherein said first food extract is a combination of the following extracts: yeast, white grape and concord grape.

* * * * *